(12) United States Patent
Hagen et al.

(10) Patent No.: US 12,071,455 B2
(45) Date of Patent: *Aug. 27, 2024

(54) MODIFIED BACTERIAL MICROCOMPARTMENT SHELL PROTEIN

(71) Applicants: The Regents of the University of California, Oakland, CA (US); BOARD OF TRUSTEES OF MICHIGAN STATE UNIVERSITY, East Lansing, MI (US)

(72) Inventors: Andrew R. Hagen, Oakland, CA (US); Cheryl A. Kerfeld, Walnut Creek, CA (US); Nancy B. Sloan, Berkeley, CA (US); Markus Sutter, Oakland, CA (US); Bryan H. Ferlez, Haslett, MI (US)

(73) Assignees: THE REGENTS OF THE UNIVERSITY OF CALIFORNIA, Oakland, CA (US); BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 154 days.

This patent is subject to a terminal disclaimer.

(21) Appl. No.: 17/458,131

(22) Filed: Aug. 26, 2021

(65) Prior Publication Data

US 2021/0395314 A1 Dec. 23, 2021

Related U.S. Application Data

(63) Continuation of application No. 16/412,133, filed on May 14, 2019, now Pat. No. 11,130,788.

(60) Provisional application No. 62/671,369, filed on May 14, 2018.

(51) Int. Cl.
| | | |
|---|---|---|
| C07K 14/195 | (2006.01) | |
| B01D 15/36 | (2006.01) | |
| B01D 15/38 | (2006.01) | |
| C07K 1/22 | (2006.01) | |
| C07K 14/315 | (2006.01) | |
| C12N 15/62 | (2006.01) | |

(52) U.S. Cl.
CPC .......... *C07K 14/195* (2013.01); *B01D 15/363* (2013.01); *B01D 15/3804* (2013.01); *C07K 1/22* (2013.01); *C07K 14/315* (2013.01); *C12N 15/62* (2013.01); *C07K 2319/70* (2013.01)

(58) Field of Classification Search
CPC .................................................. C07K 14/195
See application file for complete search history.

(56) References Cited

U.S. PATENT DOCUMENTS

| | | | |
|---|---|---|---|
| 9,547,003 B2 | 1/2017 | Howarth | |
| 11,130,788 B2 * | 9/2021 | Hagen | ............ B01D 15/3804 |
| 2012/0210459 A1 | 8/2012 | Kerfeld et al. | |
| 2013/0133102 A1 | 5/2013 | Kerfeld et al. | |
| 2014/0295520 A1 | 10/2014 | Schmidt-Dennert et al. | |
| 2015/0026840 A1 | 1/2015 | Kerfeld et al. | |
| 2016/0222068 A1 | 8/2016 | Kerfeld et al. | |
| 2017/0107523 A1 | 4/2017 | Kerfeld et al. | |
| 2018/0057546 A1 | 3/2018 | Kerfeld et al. | |

FOREIGN PATENT DOCUMENTS

| | | |
|---|---|---|
| WO | 2011/017458 A1 | 2/2011 |
| WO | 2011/094765 A2 | 8/2011 |

OTHER PUBLICATIONS

Axen et al., "A taxonomy of bacterial microcompartment loci constructed by a novel scoring method." PLoS Comput Biol 10(10):e1003898 (2014), 20 pages.
Sutter et al., "Assembly principles and structure of a 6.5-MDa bacterial microcompartment shell." Science 356(6344):1293-1297 (2017).
Tanaka et al., "Atomic-level models of the bacterial carboxysome shell." Science 319(5866):1083-1086. (2008).
Kerfeld et al., "Protein structures forming the shell of primitive bacterial organelles." Science 309(5736):936-938.(2005).
Klein et al., "Identification and structural analysis of a novel carboxysome shell protein with implications for metabolite transport." J Mol Biol 392(2):319-333 (2009).
Cai et al., "The pentameric vertex proteins are necessary for the icosahedral carboxysome shell to function as a CO2 leakage barrier." Plos One 4(10):e7521. (2009), 9 pages.
Aussignargues et al., "Bacterial microcompartment assembly: The key role of encapsulation peptides." Commun Integr Biol 8(3):e1039755 (2015), 11 pages.
Fan et al., "Short N-terminal sequences package proteins into bacterial microcompartments." Proc Natl Acad Sci U S A 107(16):7509-7514. (2010).
Kinney et al., "Elucidating essential role of conserved carboxysomal protein CcmN reveals common feature of bacterial microcompartment assembly." J Biol Chem 287(21):17729-17736 (2012).
Cameron et al., "Biogenesis of a bacterial organelle: the carboxysome assembly pathway." Cell 155(5):1131-1140 (2013).

(Continued)

*Primary Examiner* — Albert M Navarro
(74) *Attorney, Agent, or Firm* — Robin C. Chiang; LAWRENCE BERKELEY NATIONAL LABORATORY

(57) ABSTRACT

The present invention provides for a fusion protein comprising (1) a bacterial microcompartment (BMC) shell protein comprising one or more subunit, and (2) a first component of a specific-binding pair, operably linked to the BMC shell protein such that the first component faces (i) a lumen (inside) side, or (ii) outside of a BMC shell formed incorporating the fusion protein and the fusion protein does not disrupt or prevent the folding of the BMC shell protein or the ability of the BMC shell protein to integrate with other BMC shell proteins into a BMC shell; wherein the first component is capable of forming a stable or irreversible interaction with a second component of the specific-binding pair.

11 Claims, 16 Drawing Sheets

Specification includes a Sequence Listing.

(56) References Cited

OTHER PUBLICATIONS

Lawrence et al., "Evolution of coenzyme B12 synthesis among enteric bacteria: Evidence for loss and reacquisition of a multigene complex." Genetics 142(1):11-24 (1996).
Parsons et al., "Biochemical and structural insights into bacterial organelle form and biogenesis." J Biol Chem 283 (21):14366-14375. (2008).
Jakobson et al., "A systems-level model reveals that 1,2-Propanediol utilization microcompartments enhance pathway flux through intermediate sequestration." PLoS Comput Biol 13(5). (2017).
Sampson et al., "Microcompartments for B12-dependent 1,2-propanediol degradation provide protection from DNA and cellular damage by a reactive metabolic intermediate." J Bacteriol 190(8):2966-2971 (2008).
Cai et al., "Production and Characterization of Synthetic Carboxysome Shells with Incorporated Luminal Proteins." Plant Physiol 170(3):1868-1877 (2016).
Lassila et al., "Assembly of robust bacterial microcompartment shells using building blocks from an organelle of unknown function." J Mol Biol 426(11):2217-2228 (2014).
Choudhary et al., "Engineered protein nano-compartments for targeted enzyme localization." Plos One 7(3):e33342 (2012).
Jakobson et al., "De Novo Design of Signal Sequences to Localize Cargo to the 1,2-Propanediol Utilization Microcompartment." Protein Sci.26:1086-1092 (2017).
Erbilgin et al., "The Structural Basis of Coenzyme a Recycling in a Bacterial Organelle." PLoS Biol 14(3):e1002399. (2016), 20 pages.
Zakeri et al., "Peptide tag forming a rapid covalent bond to a protein, through engineering a bacterial adhesin." Proc Natl Acad Sci U S A 109(12):E690-697 (2012).
Goedhart et al., "Structure-guided evolution of cyan fluorescent proteins towards a quantum yield of 93%." Nat Commun 3:751 (2012), 9 pages.
Kremers et al., "Cyan and yellow super fluorescent proteins with improved brightness, protein folding, and FRET Forster radius." Biochemistry 45(21):6570-6580 (2006).
Dougherty et al., "Molecular genetic analysis of a plant virus polyprotein cleavage site: a model." Virology 171(2):356-364. (1989).
Griffin et al., "Specific covalent labeling of recombinant protein molecules inside live cells." Science 281(5374):269-272.(1998).
Cai et al., "The Structure of CcmP, a Tandem Bacterial Microcompartment Domain Protein from the beta-Carboxysome, Forms a Subcompartment Within a Microcompartment." J Biol Chem 288(22):16055-16063 (2013).
Larsson et al., "Crystal structures of beta-carboxysome shell protein CcmP: ligand binding correlates with the closed or open central pore." J Exp Bot 68(14)3857-3867(2017).
Price et al., "Isolation and Characterization of High CO(2)-Requiring-Mutants of the Cyanobacterium Synechococcus PCC7942 : Two Phenotypes that Accumulate Inorganic Carbon but are Apparently Unable to Generate CO(2) within the Carboxysome." Plant Physiol 91(2):514-525 (1989).
Sargent et al., "A synthetic system for expression of components of a bacterial microcompartment." Microbiology 159(Pt 11):2427-2436 (2013).
Seebeck et al., A simple tagging system for protein encapsulation. J Am Chem Soc 128(14):4516-4517 (2006).
Giessen et al., "A Catalytic Nanoreactor Based on in Vivo Encapsulation of Multiple Enzymes in an Engineered Protein Nanocompartment." Chembiochem 17(20):1931-1935 (2016).
Cai et al., "Engineering Bacterial Microcompartment Shells: Chimeric Shell Proteins and Chimeric Carboxysome Shells." ACS Synth Biol 4(4):444-453 (2015).
Menon et al., "The carboxysome shell is permeable to protons." J Bacteriol 192(22):5881-5886 (2010).
Slininger et al., "Evidence for Improved Encapsulated Pathway Behavior in a Bacterial Microcompartment through Shell Protein Engineering." ACS Synthetic Biology 6:1880-1891 (2017).
Tropea et al., "Expression and purification of soluble His(6)-tagged TEV protease." Methods in molecular biology 498:297-307 (2009).
Pettersen et al., "UCSF Chimera—a visualization system for exploratory research and analysis." J Comput Chem 25(13):1605-1612 (2004).
Kleffner et al., "Foldit Standalone: a video game-derived protein structure manipulation interface using Rosetta." Bioinformatics 33(17):2765-2767 (2017).
Lee et al., "BglBrick vectors and datasheets: A synthetic biology platform for gene expression." J Biol Eng 5:12 (2011), 14 pages.
Gibson et al., "Enzymatic assembly of DNA molecules up to several hundred kilobases." Nature methods 6(5):343-345 (2009).
Li et al., "Structural analysis and optimization of the covalent association between SpyCatcher and a peptide Tag." J Mol Biol 426(2):309-317 (2014).

* cited by examiner

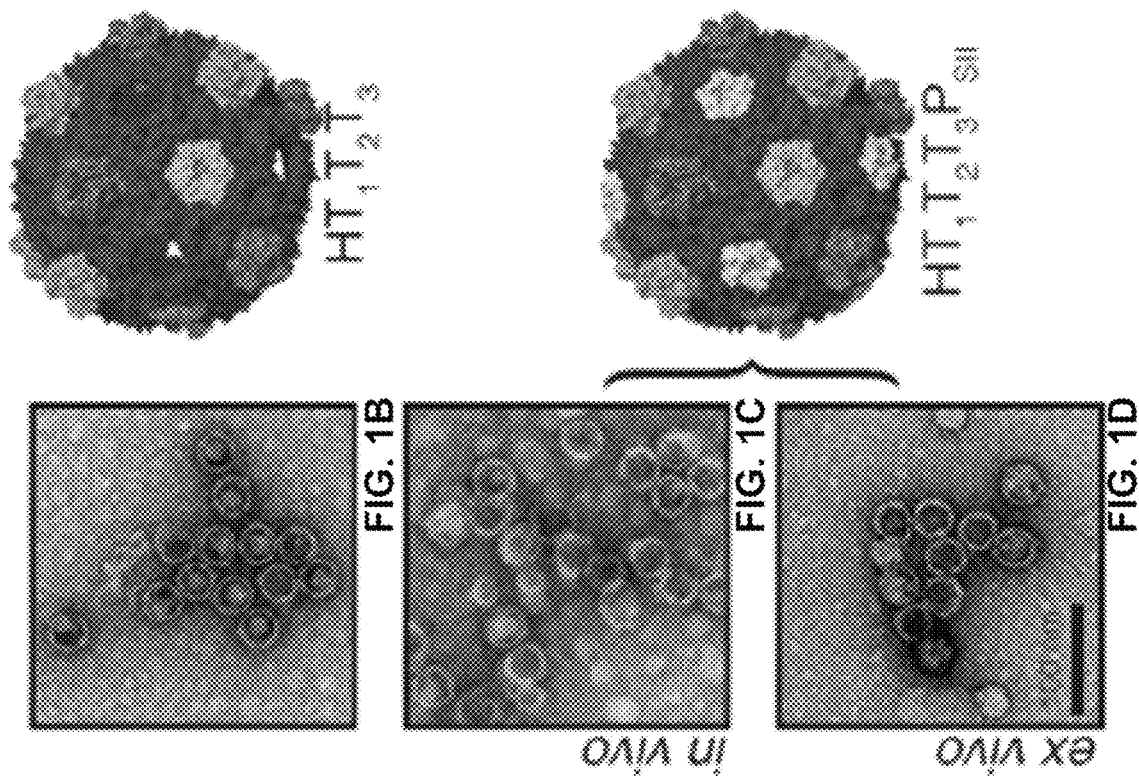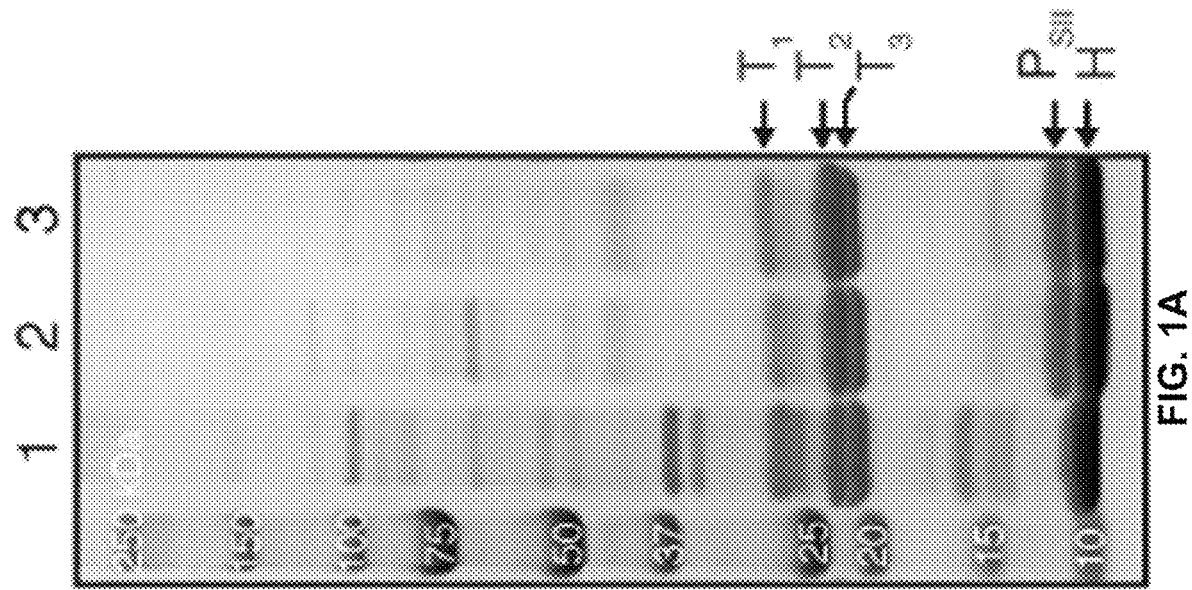

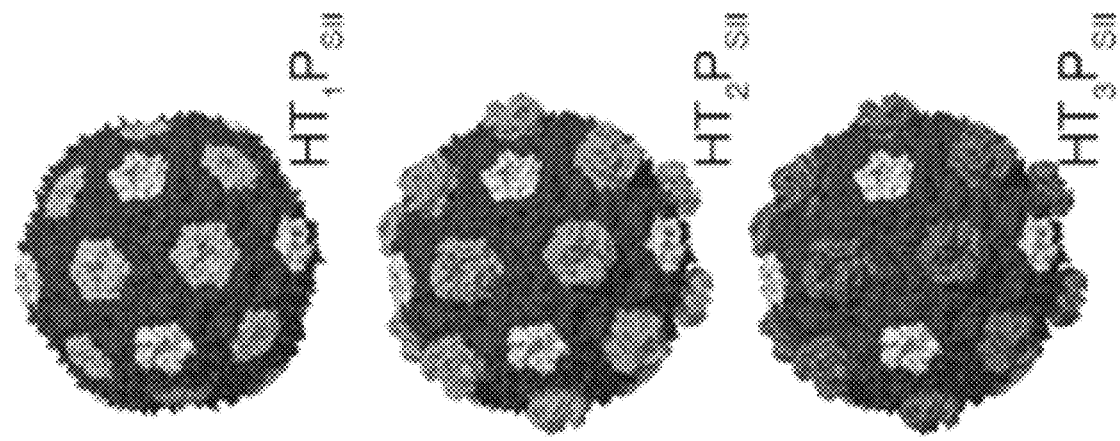
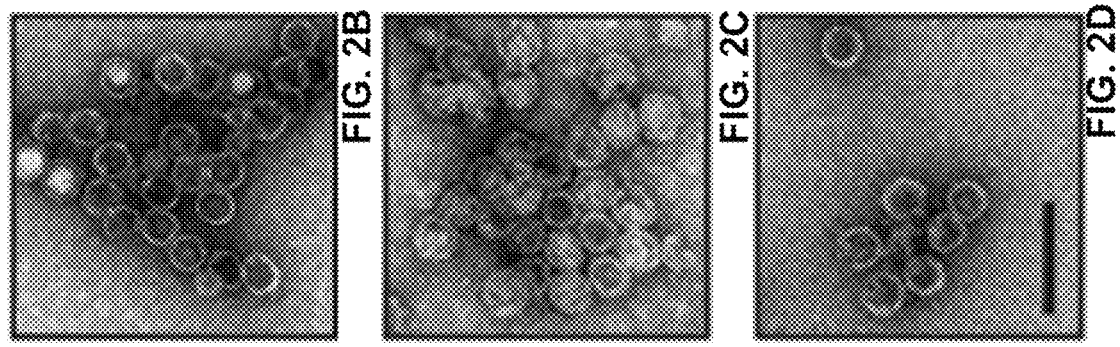
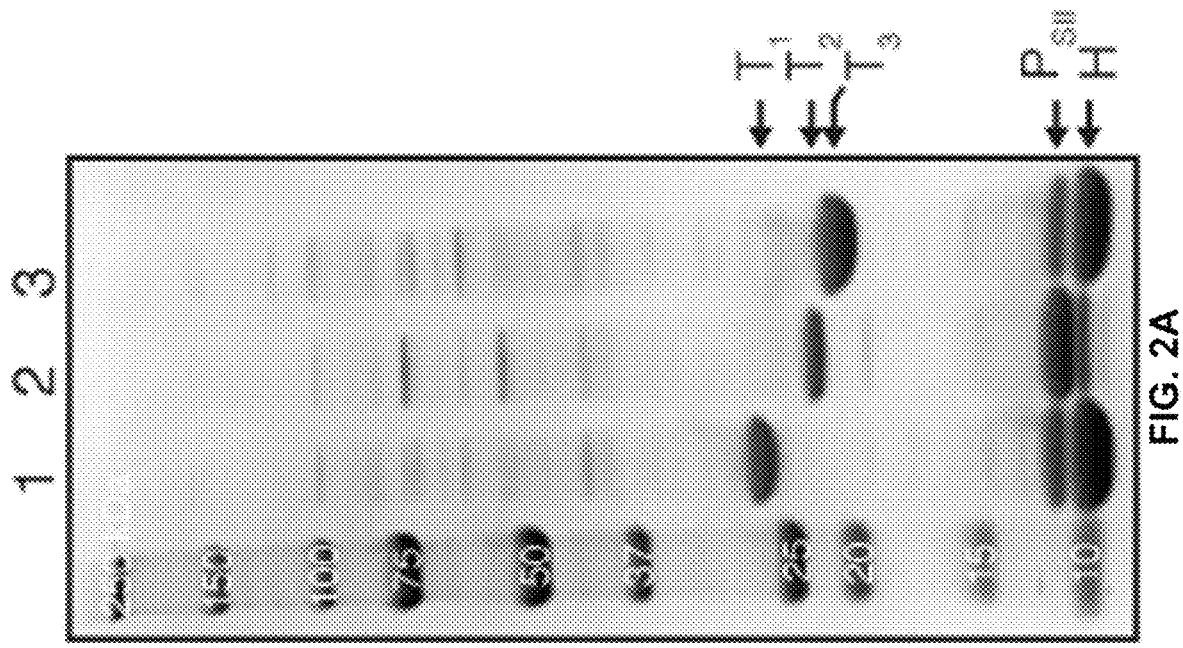

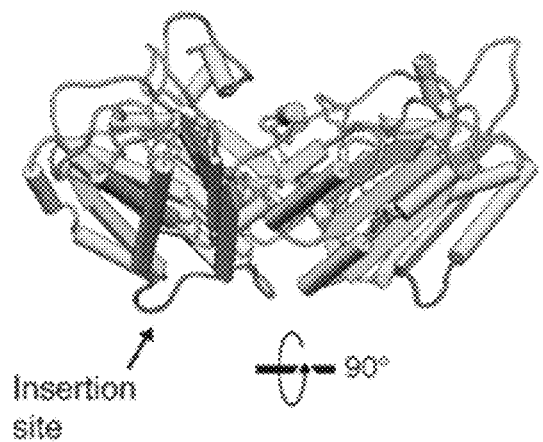
Insertion site
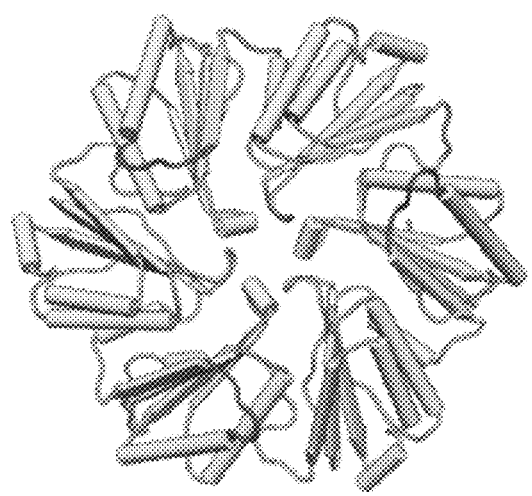
T₁
FIG. 3A
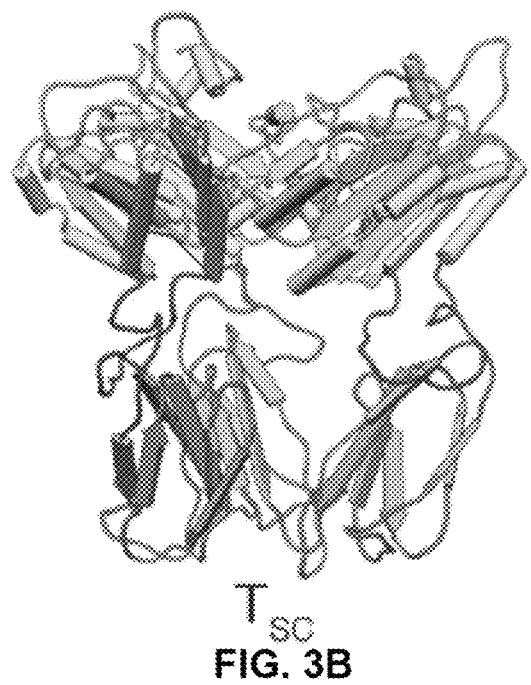
T_SC
FIG. 3B
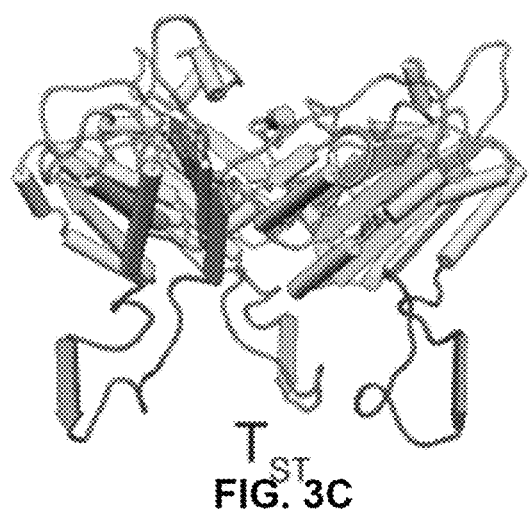
T_ST
FIG. 3C

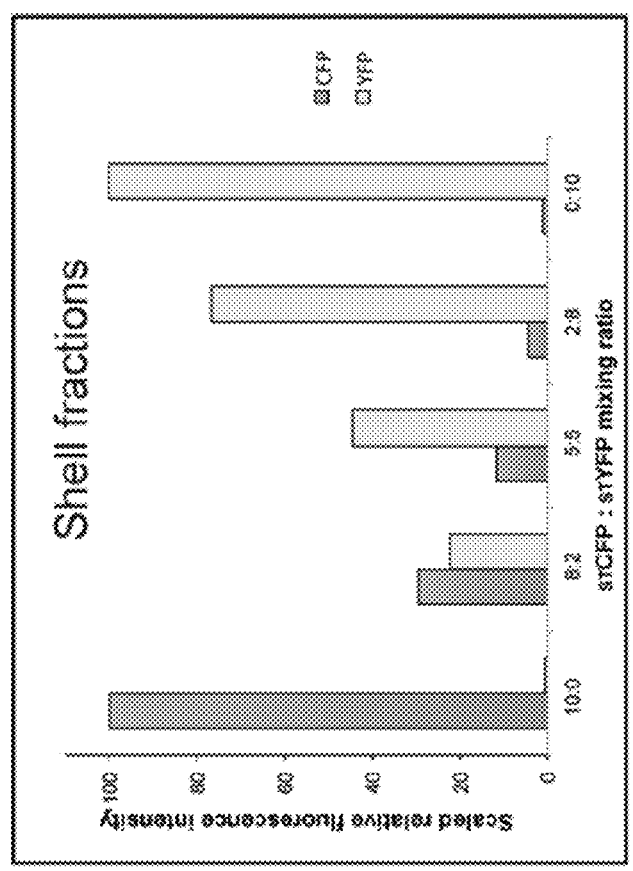
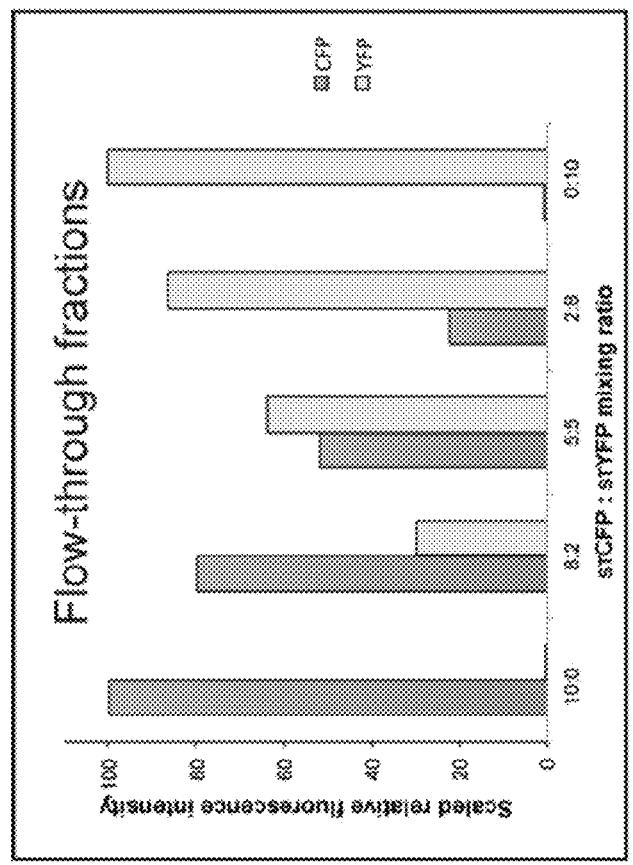
FIG. 10

FIG. 12

MODIFIED BACTERIAL MICROCOMPARTMENT SHELL PROTEIN

CROSS-REFERENCE TO RELATED APPLICATIONS

This application is a continuation application of U.S. patent application Ser. No. 16/412,133, filed May 14, 2019, which claims priority to U.S. Provisional Patent Application Ser. No. 62/671,369, filed on May 14, 2018, all of which are hereby incorporated by reference in their entireties.

STATEMENT OF GOVERNMENTAL SUPPORT

The invention was made with government support under Contract Nos. DE-AC02-05CH11231 and DE-FG02-91ER20021 awarded by the U.S. Department of Energy, and Grant No. 1R01AI114975-01 NIAID awarded by the National Institutes of Health. The government has certain rights in the invention.

FIELD OF THE INVENTION

The present invention is in the field of bacterial microcompartments (BMCs).

REFERENCE TO A "SEQUENCE LISTING" SUBMITTED AS AN ASCII TEXT FILE VIA EFS-WEB

This application contains a Sequence Listing file named "2017-131-02_Sequence_Listing_ST25" created on Dec. 9, 2019, and containing 12,288 bytes. The material contained in this text file is incorporated by reference in its entirety for all purposes.

BACKGROUND OF THE INVENTION

Bacterial microcompartments (BMCs) are ensembles of enzymes wrapped in a semi-permeable proteinaceous shell, compositionally distinguishing them from the more familiar lipid-membrane bound organelles. These compartments have been bioinformatically identified in the majority of bacterial phyla (1) where they perform distinct, spatially separate metabolic functions allowing their hosts to fix carbon, as in the anabolic carboxysomes, or metabolize substrates like ethanolamine that generate volatile or toxic intermediates, as in the catabolic metabolosomes.

The shells of all characterized BMCs include a suite of cyclically symmetric protein building blocks which are hexagonal or pentagonal in shape and which together assemble into icosahedral bodies (2, 3). The hexagons are hexa- or trimeric oligomers of a conserved, single or tandem-duplicated protein domain (pfam00936) that constitute the facets of the shell. Pentamers formed by the pfam03319 domain occupy the vertices. Pores in the hexamer and trimer (BMC-H and BMC-T) subunits mediate passage of small molecules through the shells (4, 5) and the presence of multiple BMC-H and/or BMC-T homologs with variable pore-lining residues in all characterized BMCs indicate differences in selectivity of transport amongst these subunits. In contrast to their roles in molecular selectivity, the structural necessity of multiple homologs remains underexplored. Pentamers are a minor component of shells as they occupy only the twelve vertex positions and are not thought to play a role in transport, yet are critical to the shell's function as a diffusive barrier (6). The enzyme core of BMCs is assembled into the interior of shells through non-covalent interactions between short "encapsulation peptides" (EPs) on the cargo and the lumenal side of shell proteins (7-9). A second mode of encapsulation involves "piggybacking" of EP-less enzymes via interactions with EP-harboring proteins (10).

The genetic organization of BMC core and shell proteins into superloci (1) and evidence of horizontal transfer among bacterial species (11, 12) denote BMCs as metabolic modules encoded by genetic modules. Genetic transplantation of such loci has been shown to confer novel metabolic functions to the recipient allowing, for example *Escherichia coli* to grow on 1,2-propanediol after transfer of the pdu operon from *Citrobacter freundii* (13). Indeed, repurposing BMCs to encapsulate non-native pathways could allow metabolic engineers to improve titers by increasing enzyme stability, mitigating diversion of substrates to competing pathways and sequestering potentially toxic or inhibitory intermediates (14-16). Moreover, the nanoscale dimensions and greatly improved understanding of structure and assembly principles described recently (2) suggest BMC shells are scaffolds fit for refactoring towards biomedical applications like polyvalent antigen display, drug delivery and imaging—applications that have traditionally been the purview of other nanocompartments such as virus-like particles and ferritins.

Hampering these ambitions are several technical challenges. Preparations of BMCs or BMC shells are laborious and typically result in low yields of heterogeneous particles (with some notable exceptions (17, 18)). Targeting heterologous cargo to the lumen of shells using EPs that are derived from naturally occurring BMCs is inefficient, with western blotting often required to identify cargo in shell preparations (17-20). EPs may also lead to aggregation, potentially compromising enzyme activity (21), and the binding site of EPs is unknown so cargo loading in shells is not readily programmable. Furthermore, there are no disassembly/reassembly methods developed which would allow in vitro encapsulation of cargo.

U.S. Pat. No. 9,547,003 discloses peptide tag systems that spontaneously form an irreversible link to protein partners via isopeptide bonds.

SUMMARY OF THE INVENTION

The present invention provides for a fusion protein comprising (1) a bacterial microcompartment (BMC) shell protein comprising one or more subunit, and (2) a first component of a specific-binding pair, operably linked to the BMC shell protein such that the first component faces (i) a lumen (inside) side, or (ii) outside of a BMC shell formed incorporating the fusion protein and the fusion protein does not disrupt or prevent the folding of the BMC shell protein or the ability of the BMC shell protein to integrate with other BMC shell proteins into a BMC shell; wherein the first component is capable of forming a stable or irreversible interaction with a second component of the specific-binding pair.

In some embodiments, the fusion protein comprises (1) a bacterial microcompartment (BMC) shell protein comprising one or more subunit, and (2) a first component of a specific-binding pair, operably linked to the BMC shell protein such that the first component faces a lumen (inside) side, of a BMC shell formed incorporating the fusion protein and the fusion protein does not disrupt or prevent the folding of the BMC shell protein or the ability of the BMC shell protein to integrate with other BMC shell proteins into a BMC shell; wherein the first component is capable of forming a stable or irreversible interaction with a second component of the specific-binding pair.

In some embodiments, the fusion protein comprises (1) a bacterial microcompartment (BMC) shell protein comprising one or more subunit, and (2) a first component of a specific-binding pair, operably linked to the BMC shell protein such that the first component faces outside of a BMC shell formed incorporating the fusion protein and the fusion protein does not disrupt or prevent the folding of the BMC shell protein or the ability of the BMC shell protein to integrate with other BMC shell proteins into a BMC shell; wherein the first component is capable of forming a stable or irreversible interaction with a second component of the specific-binding pair.

In some embodiments, the stable or irreversible interaction is a spontaneous formation of a covalent bond. In some embodiments, the covalent bond is an isopeptide bond (which may for example occur between a lysine and an asparagine residue in an appropriate environment).

In some embodiments, the ability of the BMC shell protein to integrate with other BMC shell proteins into a BMC shell is the ability to assemble in vitro or in vivo.

In some embodiments, the BMC shell protein subunit is BMC-H, BMC-T, or BMC-P. In some embodiments, the BMC-T shell protein subunit is $BMC-T_1$, $BMC-T_2$, or $BMC-T_3$.

In some embodiments, the first component of a specific-binding pair is a peptide. In some embodiments, the second component of the specific-binding pair is a peptide. In some embodiments, the first component of the specific-binding pair is flanked by a sequence of amino acids that adequately present the specific component to its cognate binding partner. In some embodiments, the sequence of amino acids that adequately present the specific component to its cognate binding partner is at least about one, two, three, four, five, or six glycine-serine linkers. In some embodiments, the binding between the first component and the second component of a specific-binding pair has an association constant of equal to or greater than about $10^8$ $M^{-1}$. Whether an amino acid residue of a BMC shell protein is facing inside or outside can be determined by a number of different methods. In one method, the BMC shell protein is purified and crystallized, and its three-dimensional configuration determined and compared to the structure of the shell protein in a complete shell. The amino acid residues between secondary structure elements, such as between two alpha-helices, two beta-strands, or an alpha-helix and a beta-strand are generally amenable for insertions. The residues on the concave surface of the BMC shell protein are facing inside and the amino acid residues on the convex surface of the BMC shell protein are facing outside and insertions in the loop regions of the two sides will face the respective direction (FIG. 12). In another method, the primary structure of a BMC shell protein is compared to the primary structure of a BMC shell protein having high amino acid sequence identity which three-dimensional configuration is known. The inside and outside amino acid residues from the latter can be inferred on the former.

For fusion proteins where the first component faces a lumen of the BMC shell protein, the first component is operably linked to within or adjacent to any amino acid residue of a BMC shell protein that faces the lumen or inside of a BMC shell, when the BMC shell protein is incorporated in the BMC shell. For example, when the BMC shell protein is BMC-H/HO-5815, the amino acid residues that face the lumen or inside of a BMC shell are shown in black and indicated "I" in FIG. 12. In some embodiments, when the BMC-T shell protein subunit is $BMC-T_1$, and the first component is operably linked or inserted on the lumenal side between alpha-helix two and beta-strand four of $BMC-T_1$. The first component can be operably linked or inserted on the lumenal side, or inside, of any location of any BMC shell protein subunit and tested using the methods described hererin to determine if the first component faces a lumen of the BMC shell protein and does not not disrupt or prevent the folding of the BMC shell protein or the ability of the BMC shell protein to integrate with other BMC shell proteins into a BMC shell.

For fusion proteins where the first component faces outside of the BMC shell protein, the first component is operably linked to the N-terminus, C-terminus, or within or adjacent to any amino acid residue of a BMC shell protein that faces outside (i.e. on the external surface) of a BMC shell, when the BMC shell protein is incorporated in the BMC shell. For example, when the BMC shell protein is BMC-H/HO-5815, the amino acid residueson the external surface of a BMC shell are shown in black and indicated "O" in FIG. 12. The first component can be operably linked or inserted on the outside, of any location of any BMC shell protein subunit and tested using the methods described hererin to determine if the first component faces outside of the BMC shell protein and does not not disrupt or prevent the folding of the BMC shell protein or the ability of the BMC shell protein to integrate with other BMC shell proteins into a BMC shell.

In some embodiments, the second component is linked to a "cargo", which can be any polypeptide or compound of interest. In some embodiments, the cargo can a pharmaceutical or therapeutic agent. In some embodiments, the second component, or the cargo, is an antigen capable of causing an immune response in a subject, wherein optionally the first component faces the outside. In some embodiments, the second component, or the cargo, is an antigen capable of causing an immune response in a subject such that the subject is immunized to a pathogen that comprises or presents the antigen.

In some embodiments, the first component is inserted into a shell protein at a location facing the lumen of the shell and that does not disrupt the global folding of the protein or its ability to integrate into BMC shells. The first component can also be appended to the N- or C-termini of shell proteins which project outwards from the shell in their normal context or inwards in a permuted version of the BMC-H shell protein (FIG. 12). Separately, proteins or inorganic materials that are to be encapsulated or adhered (referred to hereafter as "cargo") are fused to the first or second component, such as a short (about 13 residues) amino acid sequence (such as the amino acid sequence called "SpyTag") When co-present either in vivo or in vitro, the fusion protein (through the first component) and second component associate and form an isopeptide bond that covalently links the two polypeptides.

In some embodiments, there is the insertion of a split bacterial adhesin domain called "SpyCatcher" into a shell protein at a location facing the lumen of the shell and that does not disrupt the global folding of the protein or its ability to integrate into BMC shells. The SpyCatcher domain can also be appended to the N- or C-termini of shell proteins which project outwards from the shell in their normal context. Separately, proteins or inorganic materials that are to be encapsulated or adhered (referred to hereafter as "cargo") are fused to a short (about 13 residues) amino acid sequence called "SpyTag." When co-present either in vivo or in vitro, the SpyCatcher-shell protein and SpyTag-cargo associate and form an isopeptide bond that covalently links the two polypeptides.

In some embodiments, the first component comprises an amino acid sequence of any of the sequence taught herein. In some embodiments, the binding partner comprises an amino acid sequence of any of the sequence taught herein. In some embodiments, the first component or second combonent comprises an amino acid sequence as described in U.S. Pat. No. 9,547,003 (hereby incorporated by reference), and Zakeri, et al. *Proc. Natl. Acad. Sci.* USA, 109(12):E690-E697, 2012. In some embodiments, the first component is a receptor site and the second component is a cofactor or compound that binds of the receptor site, wherein optionally the first component faces the outside. In some embodiments, the SpyTag/SpyCatcher sequence is replaced with an "Avi-Tag" which is biotinylated by a BirA protein (either in vivo or in vitro). This can then recruit other "avidin" type proteins that bind very tightly but non-covalently to the biotin cofactor. When AviTagged proteins are used, BMC shells can be formed, and avidins are capable of binding to them.

In some embodiments, the first component faces the outside and is an affinity handle for purifying or isolating the BMC shell. In some embodiments, the second component is bound to a solid support, such as a resin, such as a resin bead or a resin column.

In some embodiments, the first component is linked to the BMC shell protein.

In some embodiments, the first component is a peptide tag and the second component is a binding partner that specifically binds to the peptide tag. In some embodiments, the first component/second component, or peptide tag/binding partner, pairs with stable or irreversible interactions by adapting a feature of amino acid chemistry, namely the spontaneous formation of isopeptide bonds (which may for example occur between a lysine and an asparagine residue in an appropriate environment).

Examples of known proteins capable of spontaneously forming one or more isopeptide bonds include Spy0128 (Kang et al, Science, 2007, 318(5856), 1625-8), Spy0125 (Pointon et al, J. Biol. Chem., 2010, 285(44), 33858-66) and FbaB (Oke et al, J. Struct Funct Genomics, 2010, 11(2), 167-80) from *Streptococcus pyogenes*, Cna of *Staphylococcus aureus* (Kang et al, Science, 2007, 318 (5856), 1625-8), the ACE19 protein of *Enterococcus faecalis* (Kang et al, Science, 2007, 318(5856), 1625-8), the BcpA pilin from *Bacillus cereus* (Budzik et al, PNAS USA, 2007, 106(47), 19992-7), the minor pilin GBS52 from *Streptococcus agalactiae* (Kang et al, Science, 2007, 318(5856), 1625-8), SpaA from *Corynebacterium diphtherias* (Kang et al, PNAS USA, 2009, 106(40), 16967-71), SpaP from *Streptococcus mutans* (Nylander et al, Acta Crystallogr Sect F Struct Biol Cryst Commum., 2011, 67(Pt1), 23-6), RrgA (Izore et al, Structure, 2010, 18(1), 106-15), RrgB (El Mortaji et al, J. Biol. Chem., 2010, 285(16), 12405-15) and RrgC (El Mortaji et al, J. Biol. Chem., 2010, 285(16), 12405-15) from *Streptococcus pneumoniae*, SspB from *Streptococcus gordonii* (Forsgren et al, J Mol Biol, 2010, 397(3), 740-51). As discussed above, any of these proteins may hence be used in the present invention to develop a peptide tag/binding partner pair.

In some embodiments, the peptide tag and binding partner pair are wherein (a) said peptide tag is a peptide fragment of an isopeptide protein, said tag having a length of at least 5 amino acids but no more than 50 amino acids, and comprises a first reactive residue involved in formation of an intramolecular isopeptide bond in an isopeptide protein, wherein said peptide tag is either unconjugated or is conjugated to a heterologous protein or peptide or to another molecule and wherein said isopeptide protein is selected from the group consisting of (i) major pilin protein Spy0128 from *Streptococcus pyogenes* as set forth in SEQ ID NO:1 or a protein with at least 95% identity thereto capable of spontaneously forming an isopeptide bond, or (ii) FbaB from *S. pyogenes* as set forth in SEQ ID NO:2, or a protein with at least 80% identity thereto capable of spontaneously forming an isopeptide bond; (b) said binding partner (i) comprises a different fragment of an isopeptide protein as set forth in (a)(i) or (a)(ii) wherein said fragment is at least 20 amino acids in length and (ii) comprises a second reactive residue involved in the isopeptide bond in said isopeptide protein, wherein the binding partner does not include the first reactive residue of the peptide tag; and (c) said peptide tag and binding partner are capable of binding to each other and forming an isopeptide bond between the first and second reactive residues.

The amino acid sequence of *Streptococcus pyogenes* major pilin protein Spy0128 is as follows:

```
                                      (SEQ ID NO: 1)
          10         20         30         40
    MKLRHLLLTG AALTSFAATT VHGETVVNGA KLTVTKNLDL 50         60         70         80
    VNSNALIPNT DFTFKIEPDT TVNEDGNKFK GVALNTPMTK 90        100        110        120
    VTYTNSDKGG SNTKTAEFDF SEVTFEKPGV YYYKVTEEKI 130        140        150        160
    DKVPGVSYDT TSYTVQVHVL WNEEQQKPVA TYIVGYKEGS 170        180        190        200
    KVPIQFKNSL DSTTLTVKKK VSGTGGDRSK DFNFGLTLKA 210        220        230        240
    NQYYKASEKV MIEKTTKGGQ APVQTEASID QLYHFTLKDG 250        260        270        280
    ESIKVTNLPV GVDYVVTEDD YKSEKYTTNV EVSPQDGAVK 290        300        310        320
    NIAGNSTEQE TSTDKDMTIT FTNKKDFEVP TGVAMTVAPY 330        340
    IALGIVAVGG ALYFVKKKNA
```

The amino acid sequence of the CnaB2 domain of *Streptococcus pyogenes* fbaB is as follows:

```
          10         20         30         40
    MTIEEDSATH IKFSKRDIDG KELAGATMEL RDSSGKTIST 50         60         70         80
    WISDGQVKDF YLMPGKYTFV ETAAPDGYEI ATAITFTVNE 90        100
    QGQVTVNGKA TKGDAHIVMV DA
```

The present invention also provides for a BMC comprising encapsulating a compound of interest.

The present invention also provides for a nucleic acid encoding the fusion protein of the present invention.

The present invention also provides for a host cell comprising the nucleic acid encoding the fusion protein of the present invention capable of expressing the fusion protein.

The present invention also provides for a two-dimensional sheet of BMC proteins comprising the fusion protein of the present invention. In some embodiments, the two-dimensional sheet of BMC proteins further comprises a corresponding second component, in a stable or irreversible interaction with of the first component of the fusion protein. In some embodiments, the two-dimensional sheet of BMC proteins comprises two or more different fusion protein wherein each fusion protein independently has a different first component that associates with a different corresponding second component. In some embodiments, each corresponding second component is associated or linked, such as covalently bound, to a different cargo or a different two-dimensional sheet of BMC proteins.

The present invention also provides for methods for making or using the fusion protein, BMC, nucleic acid, or host cell of the present invention.

The present invention also provides for a method for making a fusion protein of the present invention, the method comprising: (a) introducing a nucleic acid encoding the first component into the nucleic acid encoding a BMC shell protein to produce a nucleic acid encoding the fusion protein of the present invention, and (b) optionally expressing the fusion protein and optionally other BMC shell proteins such that the fusion protein and other shell proteins self-assemble into a BMC shell.

The present invention also provides for a method for purifying or isolating a BMC shell of the present invention, the method comprising: (a) introducing a nucleic acid encoding the first component into the nucleic acid encoding a BMC shell protein to produce a nucleic acid encoding the fusion protein of the present invention, wherein the first component faces the outside of the BMC shell protein, (b) optionally expressing the fusion protein and optionally other BMC shell proteins such that the fusion protein and the other shell proteins self-assemble into a BMC shell comprising the first component on the outside of the BMC shell, (c) contacting a composition comprising the BMC shell comprising the first component with the second component, such that the first component and the second component specifically bind to form a BMC shell-solid support complex, wherein the second component is bound to a solid support, (d) optionally separating the BMC shell from the other constituents in the composition besides the BMC shell, (e) optionally washing the BMC shell-solid support complex with a solution that does not affect the binding between the first component and the second component such that further other constituents are separated from the BMC shell-solid support complex, (f) optionally repeating the step (d) washing, and (g) optionally separating the BMC shell from the solid support by dissociating the first component from the second component. In some embodiments, the BMC shell protein of the fusion protein is a BMC-P. In some embodiments, the BMC shell protein of the fusion protein is a BMC shell protein comprising a domain which forms the pentagonal vertice of the BMC shell.

The present invention also provides for a method for titrating a range of BMC shells with variable permeability, the method comprising: (a) optionally determining a desired permeability for a BMC shell, (b) forming a series of BMC shells with a variable amount of a fusion protein, comprising a BMC-P and a first component, relative to the amounts of the BMC-H and BMC-T shell proteins, (c) optionally purifying or isolating each BMC shell formed with a specific amount of the fusion protein relative the amounts of the BMC-H and BMC-T shell proteins using a second component bound to a solid support, (d) determining the permeability of each BMC shell formed with a specific amount of the fusion protein relative the amounts of the BMC-H and BMC-T shell proteins, and (e) optionally identifying the BMC shell of step (d) that has a permeability closest to the desired permeability determined in step (a). In some embodiments, the step (b) forming comprises using a method described herein, such as in Example 1. In some embodiments, the step (b) forming comprises using an in vivo capped or ex vivo capped method.

Bacterial Microcompartments (BMCs) are selectively permeable proteinaceous organelles which encapsulate segments of metabolic pathways. A significant portion of global carbon fixation is mediated by these compartments in photosynthetic bacteria; other BMCs are involved in carbon catabolism and contribute to the fitness and virulence of some pathogenic bacteria. BMC architectures are beginning to be exploited by biotechnologists, however technical challenges including laborious purification protocols and inefficient targeting of cargo to the inside of the shells hinder engineering and characterization of these nanoparticles. These limitations are addressed through rational modifications to shell proteins which enable rapid purification of shells and precise encapsulation of cargo. These methods are applicable to functionally diverse shell systems, enabling their use in biotechnological and biomedical applications.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1A shows a comparison of different shell preparation methods. SDS-PAGE analysis of shell preparations. Lane 1: "Classic," Lane 2: In vivo capped, Lane 3: Ex vivo capped. Shell protein identities indicated by arrows.

FIG. 1B shows a negative stain TEM micrograph of a particular shell preparation and corresponding structural model (BMC-H (blue), BMC-T (green), BMC-P (yellow)). Scale bar=100 nm.

FIG. 1C shows a negative stain TEM micrograph of a particular shell preparation and corresponding structural model (BMC-H (blue), BMC-T (green), BMC-P (yellow)). Scale bar=100 nm.

FIG. 1D shows a negative stain TEM micrograph of a particular shell preparation and corresponding structural model (BMC-H (blue), BMC-T (green), BMC-P (yellow)). Scale bar=100 nm.

FIG. 2A shows a comparison of different minimal shells. SDS-PAGE analysis of crude shell preparations. Lane 1: $HT_1P_{SH}$ Lane 2: $HT_2P_{SH}$ Lane 3: $HT_3P_{SH}$ Shell protein identities indicated by arrows.

FIG. 2B shows a negative stain TEM micrograph of a minimal shell preparation and corresponding structural model. Scale bar=100 nm.

FIG. 2C shows a negative stain TEM micrograph of a minimal shell preparation and corresponding structural model. Scale bar=100 nm.

FIG. 2D shows a negative stain TEM micrograph of a minimal shell preparation and corresponding structural model. Scale bar=100 nm.

FIG. 3A shows a model of $T_1$ (wt), $T_{SC}$ and $T_{ST}$ subunits. Model of $T_1$ (PDB: 5DIH) as viewed from side of shell (top) and lumen (bottom).

FIG. 3B shows a model of $T_{SC}$ viewed from the side. Flexible coil regions colored in brown; SpyCatcher and SpyTag regions colored in grey.

FIG. 3C shows a model of $T_{ST}$ viewed from the side. Flexible coil regions colored in brown; SpyCatcher and SpyTag regions colored in grey.

FIG. 10 shows the fluorescence intensities of varying mixtures of unencapsulated and encapsulated fluorophores; Excitation/emission (nm): CFP 434/474; YFP 510/530. Left panel: Relative fluorescence intensities of flow-through fractions (unencapsulated fluorophores). Right panel: Relative fluorescence intensities of shell fractions (encapsulated fluorophores). Note attenuated emission of $_{ST}$cfp when encapsulated relative to unencapsulated $_{ST}$cfp.

Figure 12:
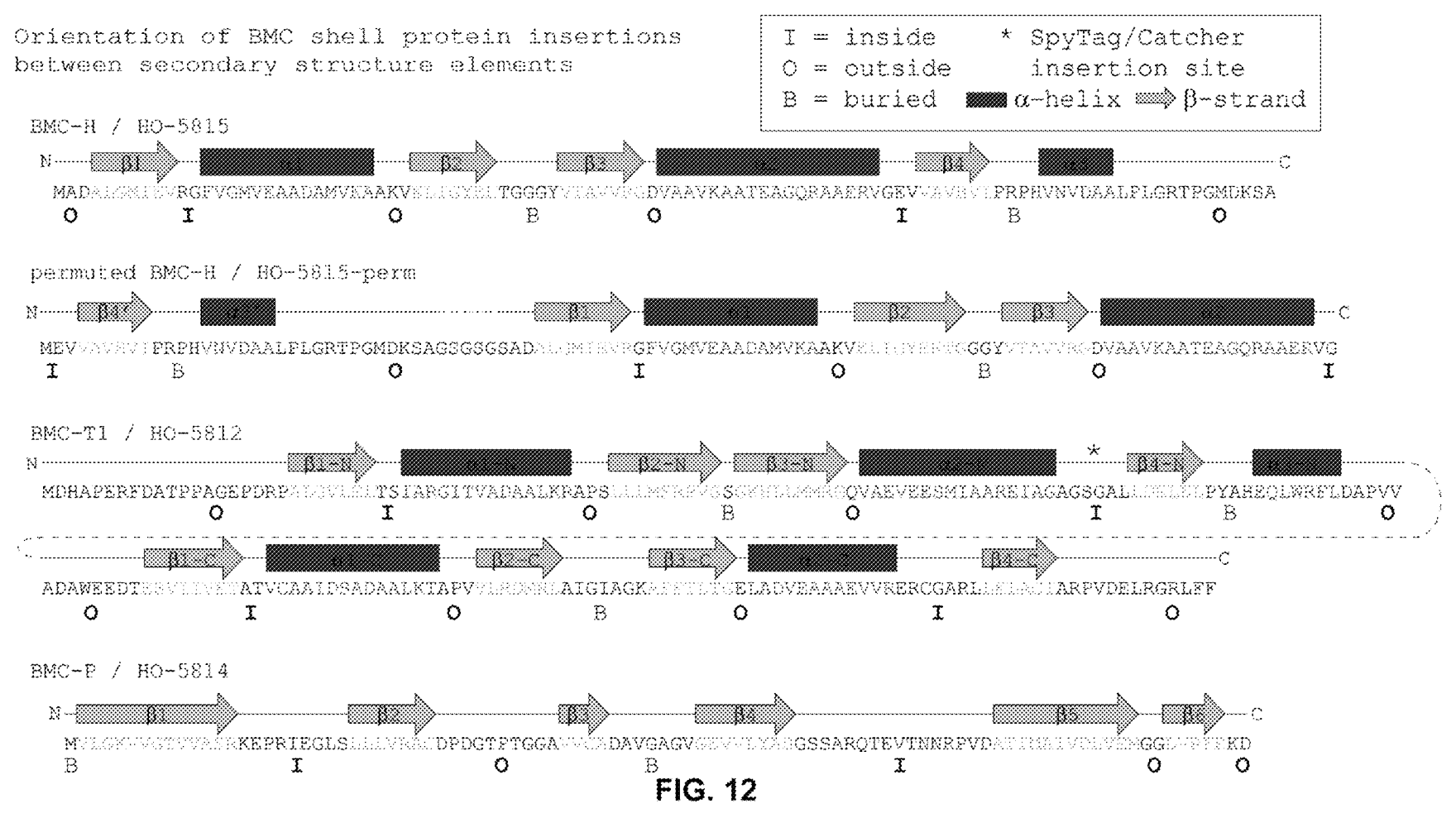

FIG. 12 shows the primary and secondary structures of BMC-H/HO-5815 (SEQ ID NO:4), a permuted version of this protein named HO-5815-perm (SEQ ID NO:5), BMC-T$_1$/HO-5812 (SEQ ID NO:6) and BMC-P/HO-5814 (SEQ ID NO:7). The topology of the proteins with specific regard to what is luminal (inside/I) and what is outside (O) of the shell is also shown as well as regions that are nor amenable for insertions because they are not accessible when the protein is integrated in the shell (B).

DETAILED DESCRIPTION OF THE INVENTION

Figure 4B:
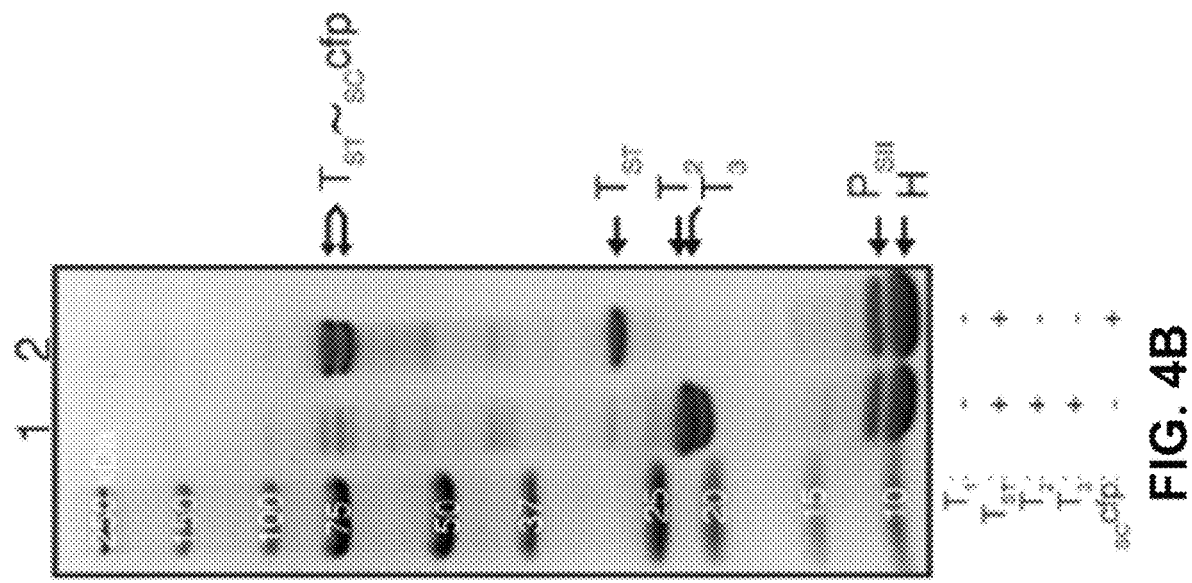
FIG. 4B shows SDS-PAGE and electron micrographs of shell and cargo preparations. SDS-PAGE of shell preparations. Composition of shell preparations given in tabular form below each lane.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

As used in the specification and the appended claims, the singular forms "a", "an", and "the" include plural references unless the context clearly dictates otherwise. Thus, for example, reference to a "shell protein" includes a single shell protein molecule, and a plurality of shell protein molecules having the same, or similar, chemical formula, chemical and/or physical properties.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" refers to a value including 10%, or one, more than the stated value and 10%, or one, less than the stated value.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

These and other objects, advantages, and features of the invention will become apparent to those persons skilled in the art upon reading the details of the invention as more fully described below.

One aspect of the present invention provides for a method to encapsulate proteins or other materials that have been fused to short peptides within the shells of Bacterial Microcompartments (BMCs) using domain insertions and split bacterial adhesin technology. In parallel or alternatively this invention may also be used to decorate the exterior of the shells and hence this technology is a generalizable way to functionalize the inside and/or outside of BMCs. This is a fundamentally different encapsulation method compared to current practices in the field which depend on fusion of encapsulation peptides (EPs) to cargo. The method described here has been shown to be superior in terms of efficiency and modularity. Robust, programmable encapsulation of cargo is essential to realize the numerous potential applications of BMCs and BMC shell proteins. Therefore this technology elevates BMCs to the pantheon of protein nanoparticles (virus-like particles, ferritins, encapsulins etc.) that may be repurposed for diverse industrial and medical uses.

Certain protein sequences used herein are described in: U.S. Pat. No. 9,547,003 B2, and Zakeri, B., Fierer, J. O., Celik, E., Chittock, E. C., Schwarz-Linek, U., Moy, V. T., & Howarth, M. (2012). In some embodiments, the peptide tag forms a rapid covalent bond to a protein, through engineering a bacterial adhesin. Proceedings of the National Academy of Sciences of the United States of America, 109(12), E690-7. Genes encoding these sequences are ordered as gene blocks through Integrated DNA Technologies. The fusion proteins and/or nucleic acids of the present invention are recombinant or constructed by human(s), or non-natural.

BMCs in general could have a number of applications in the biotech, pharmaceutical and medical industries. To realize many of these applications, efficient encapsulation of cargo as described in this invention is criticial. Apart from nanoparticles, it is demonstrated that certain shell proteins can spontaneously form two-dimensional sheets. The integration of split bacterial adhesin domains into such proteins would allow for functionalization and/or crosslinking which may imbue these sheets with interesting material properties. Metabolic engineers can target heterologous pathways to subcellular compartments (e.g. mitochondria, peroxisomes, the periplasmic space) in vivo to increase product titers by reducing competing reactions, increasing precursor pool availability, decreasing toxicity of intermediates, faster enzyme kinetics etc. As the present invention allows efficient encapsulation of cargo, this enables metabolic engineers to reliably confine heterologous pathways to BMCs which may result in concomitant titer increases. A particular advantage of protein-based organelles like BMCs in comparison to lipid-based organelles is their more molecularly defined nature. This could enable more precise control over relative stoichiometries of encapsulated enzymes in multi-step pathways, which could further increase titers. The behavior of a catalyst is sensitive to its local environment and solution state. It is shown that enzymatic biocatalysis can be improved through scaffolding-based colocalization as well as through immobilization to inert carriers (e.g. solid supports or dispersed polymers) or via cross-linking. Therefore in industrial settings, catalyst stability and/or activity may be improved by encapsulation within BMCs, adhering to the outside of BMCs or arraying enzymes on the aforementioned protein sheets. Protein-based nanocontainers such as virus-like particles (VLPs), ferritins, encapsulins etc. have attracted interest in medicine as potential polyvalent antigen scaffolds, therapeutic-delivery vehicles and imaging contrast agents. BMCs could also be used in these applications and may offer advantages conferred by the selective permeability of their shells that allow more sophisticated layers of control. For example, the present invention could allow for efficient encapsulation of therapeutic agents that are activated by a small molecule (e.g. cancer biomarker) entering the shell and interacting with an encapsulated sensor. Another example is encapsulating contrast agents or other functional nanomaterials (e.g. upconverting nanoparticles). Localization to particular tissues may be possible because the outside of the shell can be functionalized with antibodies that recognize specific cell types. Encapsulation within a shell prevents the therapeutics/material from direct interaction with the host and therefore could be more stable or less likely to provoke immune responses.

As described herein, the present invention offers significant advantages over existing encapsulation technology in terms of efficiency and precision of encapsulation. In addition, because the number of SpyCatcher docking sites per particle is known and experiments have shown near quantitative binding by SpyTagged cargo, a much higher degree of control over number of cargo molecules encapsulated per particle is realized. The same attributes will apply to functionalization of the BMC shell exterior and shell-based protein layers. Additionally, the technology is modular insofar as the SpyCatcher domain can be engineered into different shell systems and the same SpyTagged protein/material constructs can be targeted to these new systems. This offers an advantage over EP-based encapsulation which requires changing the cognate EP on the cargo each time a new system is to be used.

In a particular embodiment, the present invention comprises the insertion of a split bacterial adhesin domain called "SpyCatcher" into a shell protein at a location facing the lumen of the shell and that does not disrupt the global folding of the protein or its ability to integrate into BMC shells. The SpyCatcher domain can also be appended to the N- or C-termini of shell proteins which project outwards from the shell in their normal context. Separately, proteins or inorganic materials that are to be encapsulated or adhered (referred to hereafter as "cargo") can be fused to a short (about 13 residue) amino acid sequence called "SpyTag." When co-present either in vivo or in vitro, the SpyCatcher-shell protein and SpyTag-cargo associate and form an iso-peptide bond that covalently links the two polypeptides. For SpyCatcher insertions, the topology of the shell proteins guarantees that SpyTag-cargo are localized within the lumen of the BMC shells and are tethered in place via the isopeptide bond. In contrast, if SpyCatcher is fused to the N- or C-termini of shell proteins, the SpyTagged constructs would localize to the outside of a shell. An inverted incarnation of the method wherein SpyTag is fused to shell proteins and SpyCatcher is fused to cargo has also been demonstrated. Likewise Spytag can be fused to externally projecting shell protein termini providing a means for capture of shells using, for example, a Spycatcher functionalized matrix.

This is a fundamentally different encapsulation/functionalization method in comparison to current practices in the field which depend on fusion of so-called "encapsulation peptides" (EPs) to cargo. EPs typically consist of short (about 17 residues) polypeptide sequences that form amphipathic alpha-helices and which interact non-covalently with the inner surface of BMC shells through non-covalent hydrophobic and/or electrostatic interactions. Each different shell system (i.e. from different organisms or different biochemical subtypes) has its own EP(s) and usually undefined cognate docking site(s) on the lumenal surface of the shell. Numerous studies have shown that targeting heterologous cargo via EP fusions is rarely efficient—such heterologous cargo comprises a very minor amount of total protein in these shell preparations. In contrast, covalent association of SpyTag-cargo with SpyCatcher-shells (or the inverse) in theory offers a 1:1 stoichiometry between shell protein and cargo and therefore enables high efficiency of encapsulation and the creation of molecularly defined BMC cores/outside surfaces. The usage of split bacterial adhesin domains for bacterial micrcompartment-associated applications is novel and allows cargo to be generated independent of the shell protein (e.g. proteins expressed in a different host or use of abiotic materials).

The fundamental challenge for development of the SpyCatcher insertional fusions is identification of an architecture for the SpyCatcher domain that satisfies at least one, two or three of the following criteria:
1. Insertion at a location that is solvent exposed to the lumen, or alternatively, the exterior of BMC shells.
2. Insertion at a location that does not disrupt proper folding of the shell protein which would preclude proper integration into the greater shell structure.
3. The SpyCatcher domain is positioned such that SpyTag-cargo (or the inverse) has the steric freedom to associate and form covalent linkages.

A putative site satisfying these criteria is identified in a particular shell protein from the HO shell system found in the bacterium *Haliangium ochraceum* (locus tag: 5812) by a combination of structural analysis of the protein's solved crystal structure and sequence analysis of protein orthologs. The chosen site is a short, poorly conserved loop consisting of small, flexible amino acids of the sequence "AGSGA" (SEQ ID NO:3) which is located in the lumenal side of an assembled shell. Domain insertion is commonly done at poorly-conserved, flexible loops due the reduced chance of disrupting the target protein function in comparison to insertion within conserved, structured regions of proteins. Finally, the HO-5812 protein is homotrimeric and the insertion sites in a fully formed trimer are approximately 38.7 Angstrom apart which is speculated to be large enough to afford cargo sufficient steric freedom to associate with the SpyCatcher-fused shell protein. Because this region is shared amongst HO-5812 homologs in other shell systems (e.g. Propanediol Utilization [Pdu] and Ethanolamine Utilization [Eut] BMCs), it is believed that the methodology is amenable to application in other such shell systems.

After creation of the fusion constructs using routine molecular biology methods, tests showed unambiguously that the HO-5812-SpyCatcher and HO-5812-SpyTag fusion proteins are capable of proper integration into HO shells. Furthermore, when a respective SpyTag or SpyCatcher fused fluorescent protein is co-expressed with the shell proteins, a size-shift is observed by SDS-PAGE analysis and shell preparations are fluorescent. These two lines of evidence validate the method.

Methods of making and using BMCs, including in vitro assembly and HO shells, are taught in U.S. Patent Provisional Application Ser. No. 62/509,553; U.S. Patent Application Publication Nos. 2012/0210459, 2013/0133102, 2015/0026840, 2016/0222068, 2017/0107523, 2018/0057546; and, PCT International Patent Application Nos. WO 2011/017458 and WO 2011/094765; which are all incorporated by reference in their entireties.

CITED REFERENCES

1. Axen S D, Erbilgin O, & Kerfeld C A (2014) A taxonomy of bacterial microcompartment loci constructed by a novel scoring method. *PLoS Comput Biol* 10(10): e1003898.
2. Sutter M, Greber B, Aussignargues C, & Kerfeld C A (2017) Assembly principles and structure of a 6.5-MDa bacterial microcompartment shell. *Science* 356(6344): 1293-1297.
3. Tanaka S, et al. (2008) Atomic-level models of the bacterial carboxysome shell. *Science* 319(5866):1083-1086.
4. Kerfeld C A, et al. (2005) Protein structures forming the shell of primitive bacterial organelles. *Science* 309(5736): 936-938.
5. Klein M G, et al. (2009) Identification and structural analysis of a novel carboxysome shell protein with implications for metabolite transport. *J Mol Biol* 392(2):319-333.
6. Cai F, et al. (2009) The pentameric vertex proteins are necessary for the icosahedral carboxysome shell to function as a $CO_2$ leakage barrier. *Plos One* 4(10):e7521.
7. Aussignargues C, Paasch B C, Gonzalez-Esquer R, Erbilgin O, & Kerfeld C A (2015) Bacterial microcompartment assembly: The key role of encapsulation peptides. *Commun Integr Biol* 8(3):e1039755.
8. Fan C, et al. (2010) Short N-terminal sequences package proteins into bacterial microcompartments. *Proc Natl Acad Sci* USA 107(16):7509-7514.
9. Kinney J N, Salmeen A, Cai F, & Kerfeld C A (2012) Elucidating essential role of conserved carboxysomal protein CcmN reveals common feature of bacterial microcompartment assembly. *J Biol Chem* 287(21):17729-17736.
10. Cameron J C, Wilson S C, Bernstein S L, & Kerfeld C A (2013) Biogenesis of a bacterial organelle: the carboxysome assembly pathway. *Cell* 155(5):1131-1140.
11. Abdul-Rahman F, Petit E, & Blanchard J L (2013) The distribution of polyhedral bacterial microcompartments suggests frequent horizontal transfer and operon reassembly. *J Phylogenet Evol Biol*:1-7.
12. Lawrence J G & Roth J R (1996) Evolution of coenzyme $B_{12}$ synthesis among enteric bacteria: Evidence for loss and reacquisition of a multigene complex. *Genetics* 142 (1):11-24.
13. Parsons J B, et al. (2008) Biochemical and structural insights into bacterial organelle form and biogenesis. *J Biol Chem* 283(21):14366-14375.

14. Conrado R J, Mansell T J, Varner J D, & DeLisa M P (2007) Stochastic reaction-diffusion simulation of enzyme compartmentalization reveals improved catalytic efficiency for a synthetic metabolic pathway. *Metab Eng* 9(4):355-363.
15. Jakobson C M, Tullman-Ercek D, Slininger M F, & Mangan N M (2017) A systems-level model reveals that 1,2-Propanediol utilization microcompartments enhance pathway flux through intermediate sequestration. *PLoS Comput Biol* 13(5).
16. Sampson E M & Bobik T A (2008) Microcompartments for B12-dependent 1,2-propanediol degradation provide protection from DNA and cellular damage by a reactive metabolic intermediate. *J Bacteriol* 190(8):2966-2971.
17. Cai F, Bernstein S L, Wilson S C, & Kerfeld C A (2016) Production and Characterization of Synthetic Carboxysome Shells with Incorporated Luminal Proteins. *Plant Physiol* 170(3):1868-1877.
18. Lassila J K, Bernstein S L, Kinney J N, Axen S D, & Kerfeld C A (2014) Assembly of robust bacterial microcompartment shells using building blocks from an organelle of unknown function. *J Mol Biol* 426(11):2217-2228.
19. Choudhary S, Quin M B, Sanders M A, Johnson E T, & Schmidt-Dannert C (2012) Engineered protein nano-compartments for targeted enzyme localization. *Plos One* 7(3):e33342.
20. Jakobson C M, Slininger Lee M F, & Tullman-Ercek D (2017) De Novo Design of Signal Sequences to Localize Cargo to the 1,2-Propanediol Utilization Microcompartment. *Protein Sci.*
21. Erbilgin O, Sutter M, & Kerfeld C A (2016) The Structural Basis of Coenzyme A Recycling in a Bacterial Organelle. *PLoS Biol* 14(3):e1002399.
22. Zakeri B, et al. (2012) Peptide tag forming a rapid covalent bond to a protein, through engineering a bacterial adhesin. *Proc Natl Acad Sci* USA 109(12):E690-697.
23. Goedhart J, et al. (2012) Structure-guided evolution of cyan fluorescent proteins towards a quantum yield of 93%. *Nat Commun* 3:751.
24. Kremers G J, Goedhart J, van Munster E B, & Gadella T W, Jr. (2006) Cyan and yellow super fluorescent proteins with improved brightness, protein folding, and FRET Forster radius. *Biochemistry* 45(21):6570-6580.
25. Dougherty W G, Cary S M, & Parks T D (1989) Molecular genetic analysis of a plant virus polyprotein cleavage site: a model. *Virology* 171(2):356-364.
26. Griffin B A, Adams S R, & Tsien R Y (1998) Specific covalent labeling of recombinant protein molecules inside live cells. *Science* 281(5374):269-272.
27. Cai F, et al. (2013) The Structure of CcmP, a Tandem Bacterial Microcompartment Domain Protein from the beta-Carboxysome, Forms a Subcompartment Within a Microcompartment. *J Biol Chem* 288(22):16055-16063.
28. Larsson A M, Hasse D, Valegard K, & Andersson I (2017) Crystal structures of beta-carboxysome shell protein CcmP: ligand binding correlates with the closed or open central pore. *J Exp Bot.*
29. Price G D & Badger M R (1989) Isolation and Characterization of High CO(2)-Requiring-Mutants of the *Cyanobacterium Synechococcus* PCC7942: Two Phenotypes that Accumulate Inorganic Carbon but Are Apparently Unable to Generate CO(2) within the Carboxysome. *Plant Physiol* 91(2):514-525.
30. Sargent F, et al. (2013) A synthetic system for expression of components of a bacterial microcompartment. *Microbiology* 159(Pt 11):2427-2436.
31. Seebeck F P, Woycechowsky K J, Zhuang W, Rabe J P, & Hilvert D (2006) A simple tagging system for protein encapsulation. *J Am Chem Soc* 128(14):4516-4517.
32. Giessen T W & Silver P A (2016) A Catalytic Nanoreactor Based on in Vivo Encapsulation of Multiple Enzymes in an Engineered Protein Nanocompartment. *Chembiochem* 17(20): 1931-1935.
33. Cai F, Sutter M, Bernstein S L, Kinney J N, & Kerfeld C A (2015) Engineering Bacterial Microcompartment Shells: Chimeric Shell Proteins and Chimeric Carboxysome Shells. *ACS Synth Biol* 4(4):444-453.
34. Menon B B, Heinhorst S, Shively J M, & Cannon G C (2010) The carboxysome shell is permeable to protons. *J Bacteriol* 192(22):5881-5886.
35. Slininger Lee M F, Jakobson C M, & Tullman-Ercek D (2017) Evidence for Improved Encapsulated Pathway Behavior in a Bacterial Microcompartment through Shell Protein Engineering. *ACS Synthetic Biology.*
38. Tropea J E, Cherry S, & Waugh D S (2009) Expression and purification of soluble His(6)-tagged TEV protease. *Methods in molecular biology* 498:297-307.
39. Pettersen E F, et al. (2004) UCSF Chimera—a visualization system for exploratory research and analysis. *J Comput Chem* 25(13):1605-1612.
40. Kleffner R, et al. (2017) Foldit Standalone: a video game-derived protein structure manipulation interface using Rosetta. *Bioinformatics* 33(17):2765-2767.
41. Sutter M, Greber B, Aussignargues C, & Kerfeld C A (2017) Assembly principles and structure of a 6.5-MDa bacterial microcompartment shell. *Science* 356(6344): 1293-1297.
42. Lassila J K, Bernstein S L, Kinney J N, Axen S D, & Kerfeld C A (2014) Assembly of robust bacterial microcompartment shells using building blocks from an organelle of unknown function. *J Mol Biol* 426(11):2217-2228.
43. Lee T S, et al. (2011) BglBrick vectors and datasheets: A synthetic biology platform for gene expression. *J Biol Eng* 5:12.
44. Gibson D G, et al. (2009) Enzymatic assembly of DNA molecules up to several hundred kilobases. *Nature methods* 6(5):343-345.
45. Li L, Fierer J O, Rapoport T A, & Howarth M (2014) Structural analysis and optimization of the covalent association between SpyCatcher and a peptide Tag. *J Mol Biol* 426(2):309-317.
46. Goedhart J, et al. (2012) Structure-guided evolution of cyan fluorescent proteins towards a quantum yield of 93%. *Nat Commun* 3:751.
47. Kremers G J, Goedhart J, van Munster E B, & Gadella T W, Jr. (2006) Cyan and yellow super fluorescent proteins with improved brightness, protein folding, and FRET Forster radius. *Biochemistry* 45(21):6570-6580.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Programmed Loading, Rapid Purification and Permeability Studies of Engineered Bacterial Microcompartment Shells Bacterial Microcompartments (BMCs) are selectively permeable proteinaceous organelles which encapsulate segments of metabolic pathways in numerous bacterial phyla. They consist of an enzymatic core surrounded by a protein shell composed of multiple distinct proteins. Despite great potential in varied biotechnological applications, engineering efforts have been stymied by technical challenges including difficulties in isolation and characterization of these particles as well as a dearth of robust and precise methods for controlling core composition and shell permeability. In this study, we address these challenges by functionalizing shell proteins with affinity handles (CAP) and specific cargo docking sites (EnCo), enabling facile purification and defined cargo loading. The affinity handles were used to rapidly screen for shell formation, revealing a remarkable plasticity in shell subunit composition. By tethering a novel fluorescence-based probe within the shell we assayed permeability at the protein and small molecule scale. These shell functionalizations are here used to extend our knowledge of BMC architectural principles and enable the development of minimal shell systems of precisely defined structure and composition. The generalizability of EnCo and CAP will enable their application to functionally diverse organelles to facilitate both characterization of natural functions and the development of bespoke shells for selectively compartmentalizing proteins.

Here, through rational modifications to shell proteins in our model BMC system HO (from *Haliangium ochraceum*), we report the development of the CAP and EnCo methods. Complementation-based Affinity Purification (CAP) enables facile screening of assembly and rapid purification of shells. We apply this method to demonstrate a remarkable plasticity of subunit composition in our model shell system. Encapsulation via Covalent-linkage (EnCo) is used to robustly program multiple cargo species into shells at predictable ratios both in vivo and ex vivo, enabling the encapsulation of heterologously produced cargo and abiotic materials. Finally, we apply a fluorescence-based probe to assess the permeability of our engineered shells and find they maintain their barrier functionality against macromolecular species while permitting ingress of a small molecule—likely through the pores of one or more shell proteins. These methodological advances should be applicable to other BMC systems, simplifying and accelerating assembly and permeability studies as well as elevate BMC shells to the pantheon of well-characterized and engineerable nanoparticles, enabling their application towards metabolic engineering and biomedical applications.

Results

Homogeneous Shells Lacking Pentamers Can Be Capped and Pulled-Down Via Affinity Chromatography To obtain a crystal structure of synthetic BMC shells it was necessary to supplement shells with additional copies of the pentamer-forming proteins. This suggests substoichiometric production of pentamer during expression of the HO shell synthetic operon (2). Previously we had observed that facets assembled into 3-dimensional particles independent of presence of pentamers (18); taken together, these findings suggested a strategy for producing shells lacking vertices that could be subsequently capped and purified.

We hypothesized that appending a high affinity, specific tag such as the Strep-II sequence to the pentamer would enable pull-downs of shells after capping. Additionally, affixing the ten residue, 1.2 kDa Strep-II tag to the pentamer would result in a size shift allowing it to be resolved from the 10.1 kDa hexamer protein via SDS-PAGE analysis. These combined properties would enable rapid purification and analysis of complete and cargo-loaded shells by obviating the need for laborious and technically demanding density gradient ultracentrifugation and ion-exchange chromatography steps.

We validated this hypothesis by comparing "classically" (2, 18) prepared $HT_1T_2T_3$ shells to $HT_1T_2T_3P_{SII}$ shells prepared by two novel methods. In the first method, which recapitulates normal in vivo assembly of shells, $P_{SII}$ proteins were co-expressed from a secondary plasmid in the same strain, and then purified via a StrepTrap column (see methods for details). In the second method, the crude lysate of the $HT_1T_2T_3$ expressing strain was mixed with the crude lysate of a separate strain expressing $P_{SII}$ for "ex vivo" capping and after a brief incubation, clarified and purified via StrepTrap. Excess $P_{SII}$ proteins and trace contaminants were subsequently removed via anion-exchange chromatography. FIG. 1A shows, $HT_1T_2T_3P_{SII}$ shells are obtained when either the in vivo (lane 2) or ex vivo (lane 3) capping/pull-down methods are employed according to SDS-PAGE analysis. We observe no morphological changes to our affinity-purified shells (FIG. 1B to FIG. 1D), indicating that the Strep-tag is well-tolerated. Notably, the CAP-purified shells obtained are higher in purity compared to classically prepared $HT_1T_2T_3$ shells (lane 1), and the entire protocol from cell pellets to shells can be performed in a matter of hours.

It is unclear why there are subtle differences in the abundance of contaminants between lanes 2 and 3 (e.g. the band migrating between 50 and 75 kDa), however these observations are reproducible and may arise from the different plasmid content of the strains used (a double-transformed strain vs. a mixture of two singly-transformed strains). Nevertheless, the classically prepared shells are approximately 70% pure whereas both CAP-purified shell preparations are >95% pure and the entire protocol from cell pellets to shells can be performed in a matter of hours. In addition, the final yield of shells for the different methods is similar, ranging from 0.40 to 0.55 milligram purified shell per gram cell pellet. Control reactions using a pentamer variant without the SII tag fail to appreciably recover shells during the ex vivo CAP protocol, indicating that the method is dependent on specific interactions with the affinity resin.

Analysis of the initial ex vivo capping experiment suggested that at the 1:2 (v/v) mixing ratio of pentamer lysate to shell lysate used, the pentamers are present in stoichiometric excess (i.e. greater than twelve pentamer subunits per shell particle). This is evidenced by a substantial peak comprised primarily of pentamer protein which elutes prior to the capped shells during the anion-exchange chromatography run. While we cannot be certain at this stage that every vertex is occupied when pentamers are in such excess, we nonetheless performed a pentamer titration to determine if putative sub-stoichiometric amounts of pentamer provide sufficient avidity to pull-down the (presumably) partially capped shells. Equal volumes of shell lysates were mixed with a range of pentamer lysate amounts (as low as 1:160 pentamer to shell volumetric mixing) and CAP-purified. The eluates were subjected to SDS-PAGE analysis, this time without anion-exchange polishing steps in order to preserve the relative ratios of all eluted proteins. Decreasing pentamer to hexamer band intensities in tandem with decreased pentamer loading indicate that sub-stoichiometric amounts of pentamer are still able to recover shells and overall impact on shell yield is modest above a certain pentamer loading threshold. We attribute the trace amounts of shells recovered in the no-pentamer control lane to incomplete elution of pentamers and/or shells from previous StrepTrap chromatography runs. Together, these results indicate that partially capped shells maintain sufficient avidity to be CAP-purified—a property that may be applied toward rapid purification of shells that can still be loaded with cargo ex vivo through the remaining pentamer vacancies and then fully capped.

Finally, we show that other shell systems are amenable to affinity-based purification by appending a Strep-II tag to the pentameric CcmL protein in a synthetic operon used to produce beta-carboxysomal shells from *Halothece* sp. PCC 7418[17] ("Halo" hereafter). As with the in vivo CAP described above, proteins were heterologously expressed in *E. coli* and purified by StrepTrap and anion-exchange. Highly pure, morphologically homogeneous particles are obtained via affinity purification. In the native systems, the absence of CcmL typically results in elongated carboxysomes; the presence of pentamer seems to be required for the termination of facet growth[10,29]. Accordingly, uncapped synthetic carboxysome shells cannot be complemented in trans as in the ex vivo CAP method used for HO shells. Nevertheless, the rapid isolation of BMCs of a completely different type suggests the method may be broadly applicable to other shells systems.

CAP Enables Rapid Screening of Shell Formation to Define a Minimal Shell Composition Recent work in our lab (2) revealed HO shells to be T=9 icosahedra with one of the three possible BMC-T proteins occupying the central position of each facet. Due to high shape complementarity between the trimers despite significant primary sequence divergence we predicted that the trimers would be interchangeable. We therefore employed CAP to screen for the potential formation of shells comprised of the hexamer, one of the three trimers, and the pentamer protein. Shells were produced by expression from three plasmids each bicistronically expressing the hexamer and a single trimer. Because we were employing this method as a facile screen for shell assembly, we omitted subsequent anion-exchange polishing steps. Consequently, by ensuring $P_{SII}$ protein is in stoichiometric excess and equally applied to each $HT_n$ lysate, densitometric analysis of the $P_{SII}$ to hexamer band intensity ratios gives a crude measure of relative shell yields (SDS-PAGE samples are loaded based on normalized A280 values).

As shown in FIG. 2A, expression of any single BMC-T domain with BMC-H is sufficient to form shells as assayed by CAP. To our knowledge, this is the first demonstration of shell formation from just a single species each of hexamer, trimer and pentamer proteins. Because identical trimers occupy each facet in these minimal shells, it is also the first isolation of BMC shells that are molecularly defined icosahedra. Interestingly, the $P_{SII}$ to BMC-H ratios reveal notable differences between the band intensities of the three shell preparations. Whereas shells comprised of just $T_1$ and $T_3$ trimers ($HT_1P_{SII}$ and $HT_3P_{SII}$, respectively) show similar pentamer:hexamer ratios (lanes 1 and 3), the yield of $HT_2P_{SII}$ shells is markedly reduced as indicated by a lower hexamer:pentamer band-intensity ratio. Whether this is attributable to the impact a particular BMC-T has on shell assembly efficiency or is merely an artifact of differential expression/stability between the trimers remains undetermined. We note no major morphological differences in these minimal shell preparations, further reinforcing the notion that each individual trimer serves identical structural roles within the context of the shell architecture, despite their presumed differences in permeability (FIG. 2B to FIG. 2D).

EnCo: A Novel Encapsulation Method Enables Robust Encapsulation of Cargo

To-date, published encapsulation methods have been inefficient (17-20). We sought a synthetic route to encapsulation that circumvents the shortcomings of EPs by using the SpyTag/SpyCatcher split bacterial adhesin system (22). This technology relies on genetically fusing a 9 kDa "SpyCatcher" domain to one protein partner and a 13 residue "SpyTag" to another protein partner. When the SpyCatcher and SpyTag polypeptides encounter one another, an isopeptide bond autocatalytically forms between them, covalently linking the two partner proteins. We reasoned that a SpyCatcher or SpyTag localized to the lumen of a BMC shell would serve as a defined docking site for cargo protein tagged with SpyTag or SpyCatcher (respectively).

$T_1$ was chosen as a target for insertional mutagenesis of the SpyTag and SpyCatcher sequences (see methods for detailed design considerations). As shown in FIG. 3A, a region was identified on the lumenal side between alpha-helix two and beta-strand four, which is not predicted to make any contacts with neighboring shell proteins and which lies approximately 24 Å from the subunit's central pore (the entire subunit is approximately 70 Å edge-to-edge). This spacing from the three-fold symmetry axis of the subunit mitigates the possibility of steric clashes from inserted/conjugated domains which could prevent the assembly of individual protomers into the trimeric subunit and/or result in incomplete cargo conjugation. SpyCatcher and SpyTag, flanked by six residue glycine-serine linkers, were inserted into $T_1$ to create "$T_{SC}$" and "$T_{ST}$" constructs, respectively (FIG. 3B and FIG. 3C).

The wildtype $T_1$ was replaced with the $T_{SC}$ mutant in plasmids that express the full complement of trimers ($pHT_1T_2T_3$) as well as the "minimal shell" producing $pHT_1$ plasmid to create, respectively $pHT_{SC}T_2T_3$ and $pHT_{SC}$. SpyTag was appended to the N-terminus of the cyan fluorescent protein mTurquoise2 (23) and cloned into a compatible and orthogonally inducible plasmid with a C-terminal hexahistidine tag ("$_{ST}$cfp").

Figure 7A:
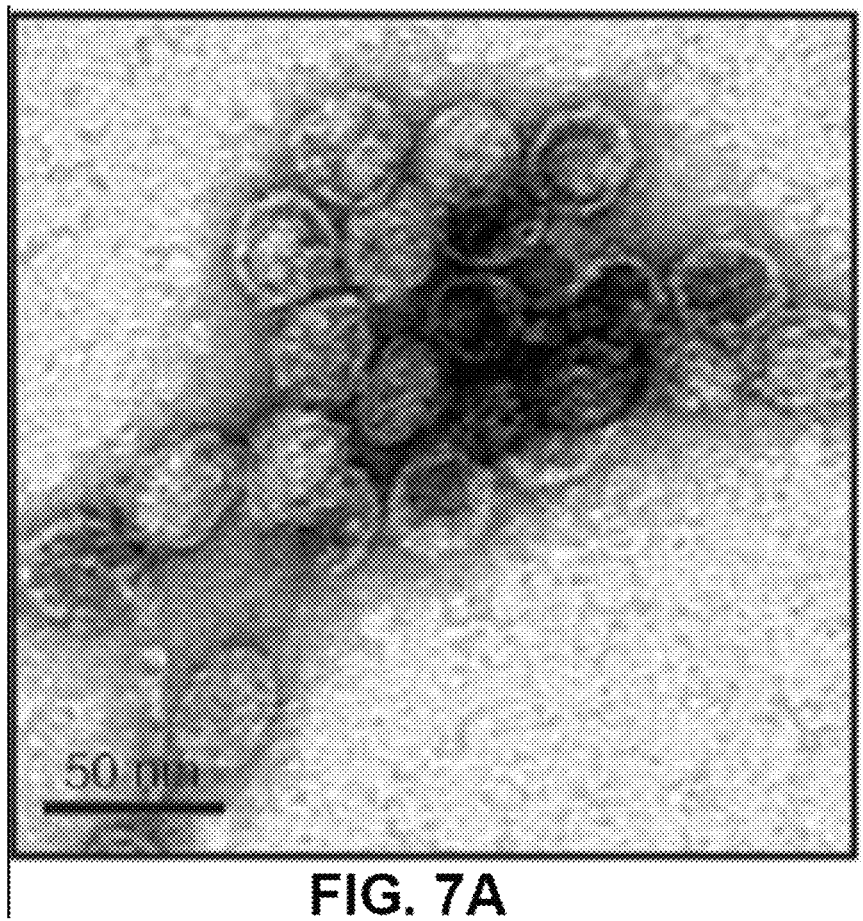
FIG. 7A shows a characterization of various shell preparations. TEM analysis of $HT_{SC}\sim_{ST}cfpT_2T_3P_{SII}$ shells revealing normal morphology.
Figure 7B:
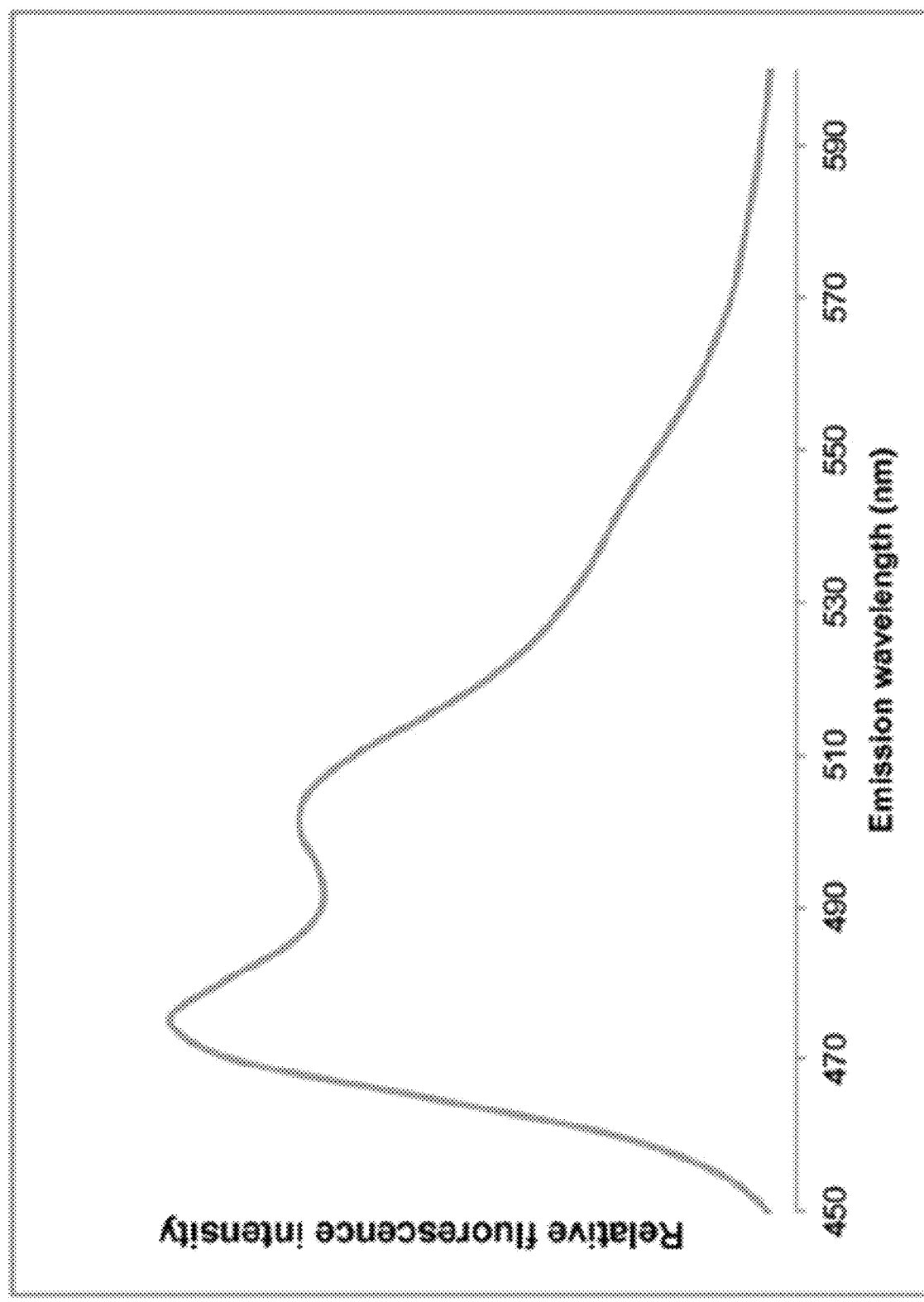
FIG. 7B shows a characterization of various shell preparations. Representative emission spectrum of $_{ST}$cfp-loaded shells ($HT_{SC}\sim_{ST}cfpP_{SII}$ shells, excitation: 405 nm).

Shell and cargo plasmids were co-transformed and shell expression was induced either with or without simultaneous induction of $_{ST}$cfp cargo. CAP was then used to isolate the resultant shells. SDS-PAGE analysis of unpolished eluates is shown in FIG. 4A. In contrast to the wildtype shells in lane 1 in which the wildtype $T_1$ protein is detected at its normal relative abundance, the $T_{SC}$ is undetectable in the putative $HT_{SC}T_2T_3P_{SII}$ shells. However in lane 3, the fused $T_{SC}\sim_{ST}$cfp trimer, which migrates at approximately 75 kDa, is observed—likely due to the increase in the protein mass upon conjugation to cargo allowing the fusion to exceed the stain's limit of detection. This would suggest that the $T_{SC}$ protein is at a modest competitive disadvantage for integration into shells compared to wildtype $T_1$ and $T_2/T_3$ and/or is a reflection of the somewhat attenuated solubility of $T_{SC}$ relative to $T_1$ (data not shown). Nevertheless, these $HT_{SC}\sim_{ST}$cfp$T_2T_3P_{SII}$ shells exhibit normal morphology by microscopic analysis and have a fluorescence emission spectrum consistent with mTurquoise2 (FIG. 7A and FIG. 7B), thus proving that cargo-fused $T_{SC}$ can integrate into shells without any gross morphological disruption. Furthermore, whereas EP-based encapsulation in the HO shell system (among others) requires western blotting to detect cargo, the detection of loaded cargo by coomassie stain alone represents a significant improvement over existing methods.

Figure 7C:
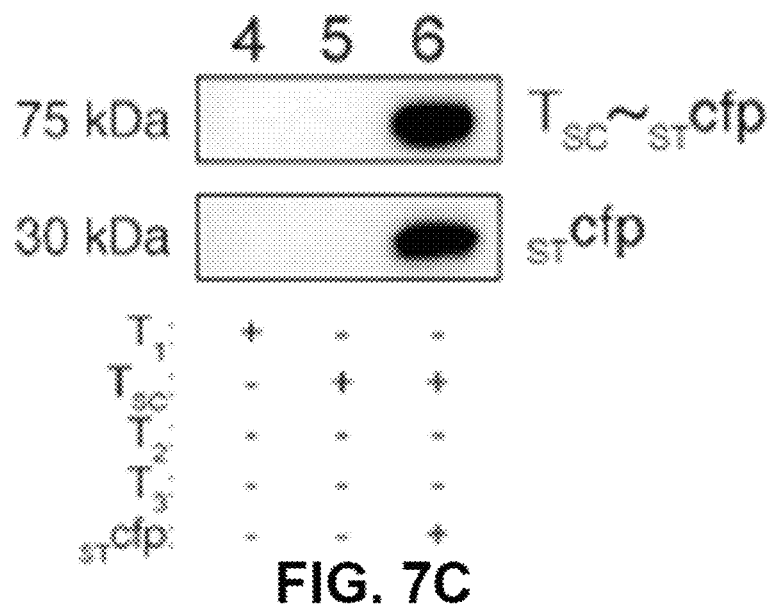
FIG. 7C shows a characterization of various shell preparations. anti-His western blot of a subset of shell preparations. Composition of shell preparations given in tabular form below each lane; lane numbers correspond to those in FIG. 4A.

Minimal shells harboring only the $T_{SC}$ subunit have more cargo binding capacity due to the absence of competition for the trimer subunit position with $T_2$ and $T_3$ proteins—a theoretical 60 copies of cargo could be recruited by the twenty trimeric subunits. This was confirmed by characterizing cargo loading using the pHT$_{SC}$ plasmid and results are shown in FIG. 4A lanes 4-6. Lane 5, in which expression of cargo is not induced, now reveals the presence of $T_{SC}$ as expected (lest no shells be formed) and excitingly, lane 6 shows the $T_{SC}$ band is nearly completely converted to the cargo-fused $T_{SC}$~$_{ST}$cfp form in these shell preparations. Interestingly, a small amount of free $_{ST}$cfp co-purifies with the shells (lane 6) which could be a result of stochastic encapsulation or proteolytic "deconjugation" from $T_{SC}$. Western blotting against the hexahistidine tag present in $_{ST}$cfp confirms the identity of these proteins and reveals that the faint band at ~75 kDa in lane 5 is a contaminant and not $T_{SC}$~$_{ST}$cfp which could result from leaky expression of the $_{ST}$cfp in the absence of inducing agent (FIG. 7C).

Figure 4A:
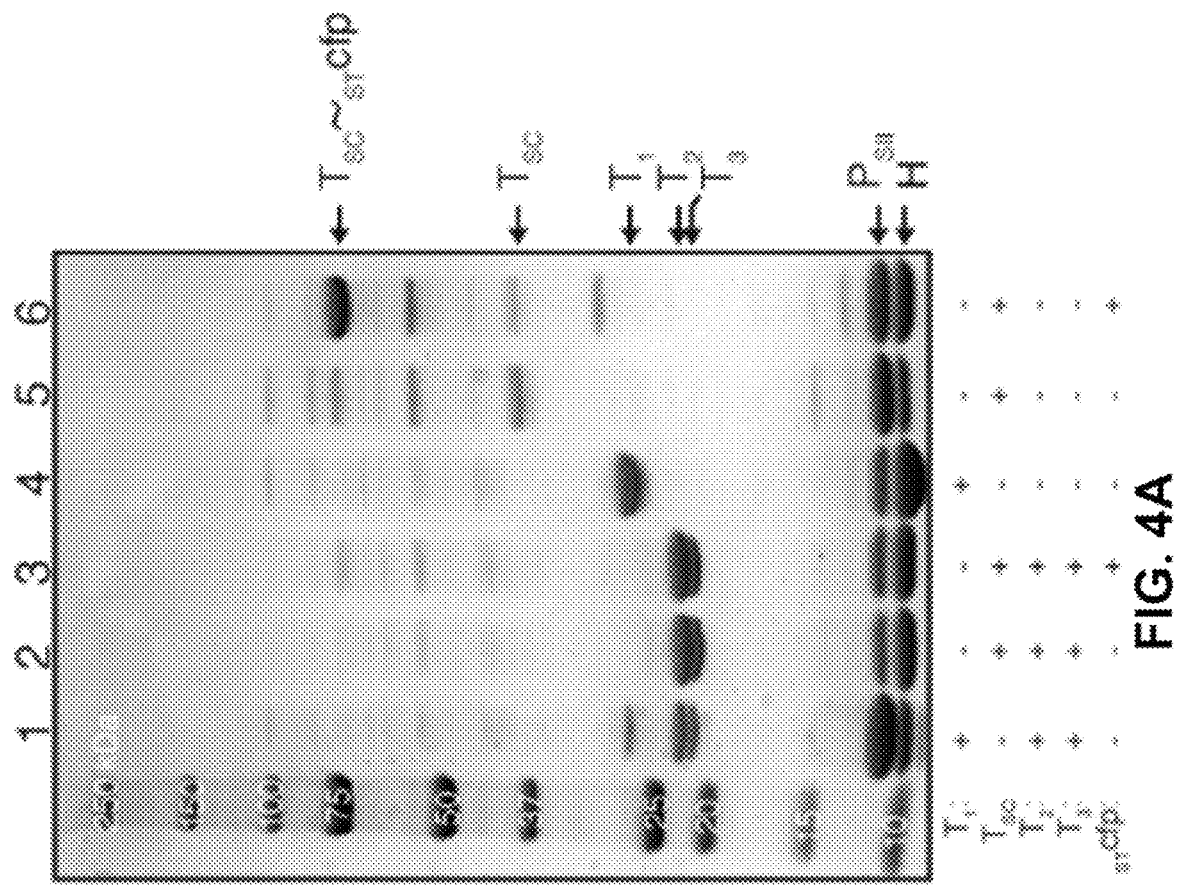
FIG. 4A shows SDS-PAGE and electron micrographs of shell and cargo preparations. SDS-PAGE of shell preparations. Composition of shell preparations given in tabular form below each lane.
Figure 4C:
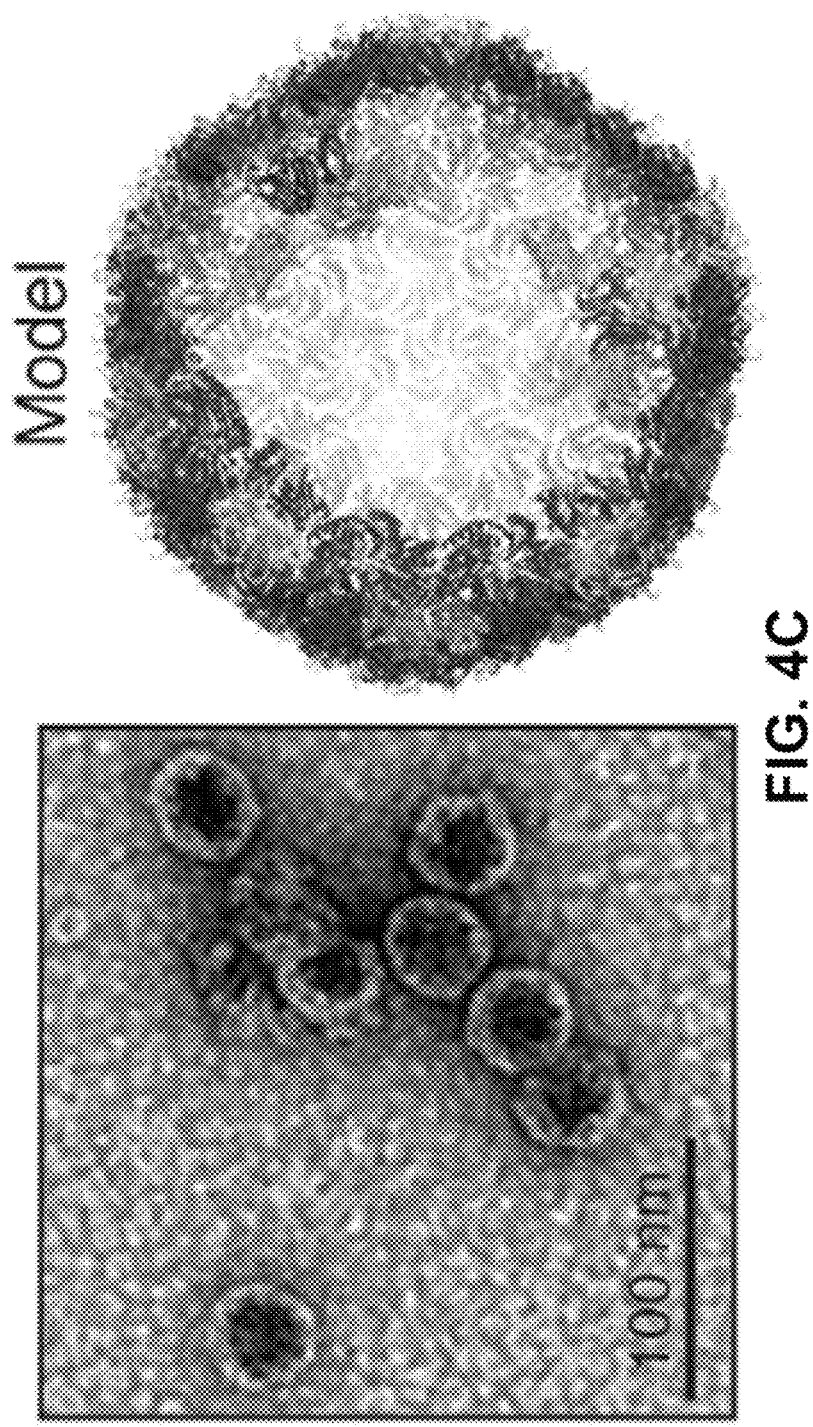
FIG. 4C shows a negative stain TEM of $HT_{SC}\sim_{ST}cfpP_{SII}$ shell preparation (corresponds to lane 6 of FIG. 4A), and a cutaway model of shells (cfp rendered in turquoise, not completely functionalized for clarity).

When SpyTag is inserted into $T_1$ and SpyCatcher fused to cargo (i.e. the inverse arrangement), similar behavior is observed in the context of full shells: the $T_{ST}$~$_{SC}$cfp fusion is detected but not at the relative abundance expected in wildtype $HT_1T_2T_3P_{SH}$ shells (FIG. 4B lane 1). However, in comparison to the minimal $HT_{SC}$~$_{ST}$cfpP$_{SH}$ shells in FIG. 4A lane 6, a significant fraction of the $T_{ST}$ subunit remains unconjugated to the $_{SC}$cfp cargo (FIG. 4B lane 2). This could indicate that the $T_{ST}$ is less efficient at recruiting cargo compared to $T_{SC}$ and/or that SpyCatcher-fused cargo is sterically frustrated from productive binding to the $T_{ST}$ subunit. A final, non-mutually exclusive scenario is that shells form prior to cargo recruitment and the larger $_{SC}$cfp (42.7 kDa) is less able to transit the pentamer vacancies compared to $_{ST}$cfp (29.9 kDa). $HT_{ST}$~$_{SC}$cfpP$_{SH}$ shells are obtained at levels similar to $HT_1T_2T_3P_{SH}$ shells (0.40 mg per gram of cell pellet) while $HT_{SC}$~$_{ST}$cfpP$_{SH}$ shells incur a significant reduction in yield (0.04 mg per gram cell pellet), though purity is comparable after anion-exchange chromatography is performed. Finally, we calculated the number of cfp cargo proteins per shell using fluorescence intensity values and find that $HT_{SC}$~$_{ST}$cfpP$_{SH}$ shells have approximately 73 copies per shell and $HT_{ST}$~$_{SC}$cfpP$_{SH}$ shells have approximately 58 copies per shell. These numbers are in reasonable agreement with theoretical estimates based on percent conversion of the trimers to their respective conjugates as observed in SDS-PAGE analysis.

Figure 8:
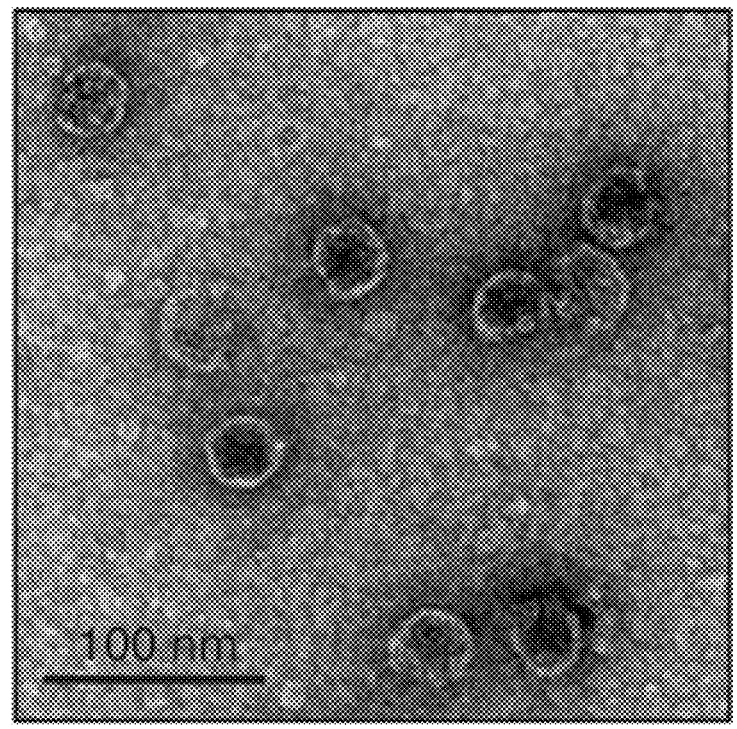
FIG. 8 shows TEM analysis of unloaded minimal Spy-Catcher shells ($HT_{SC}P_{SII}$).

Based on the assembly principles and structure of HO shells reported by Sutter et al (2), the minimal shells in lanes 4-6 harbor twenty trimer subunits, nearly all of which are conjugated to cargo in the $HT_{SC}$~$_{ST}$cfpP$_{SH}$ shell preps according to the aforementioned SDS-PAGE analysis. This should roughly double the apparent shell thickness at the twenty trimer positions and indeed, examination of transmission electron micrographs of the minimal shell compositions depicted in FIG. 4A lane 6 reveal notable differences in shell appearance: cargo-loaded shells appear thicker and more stippled compared to $HT_1P_{SH}$ shells (FIG. 2A) as well as "empty" $HT_{SC}P_{SH}$ shells (FIG. 8). Together, these findings validate EnCo as a robust method for encapsulation of cargo into morphologically undisrupted shells using trimer subunits functionalized with molecular traps.

Figures 9A, 9B:
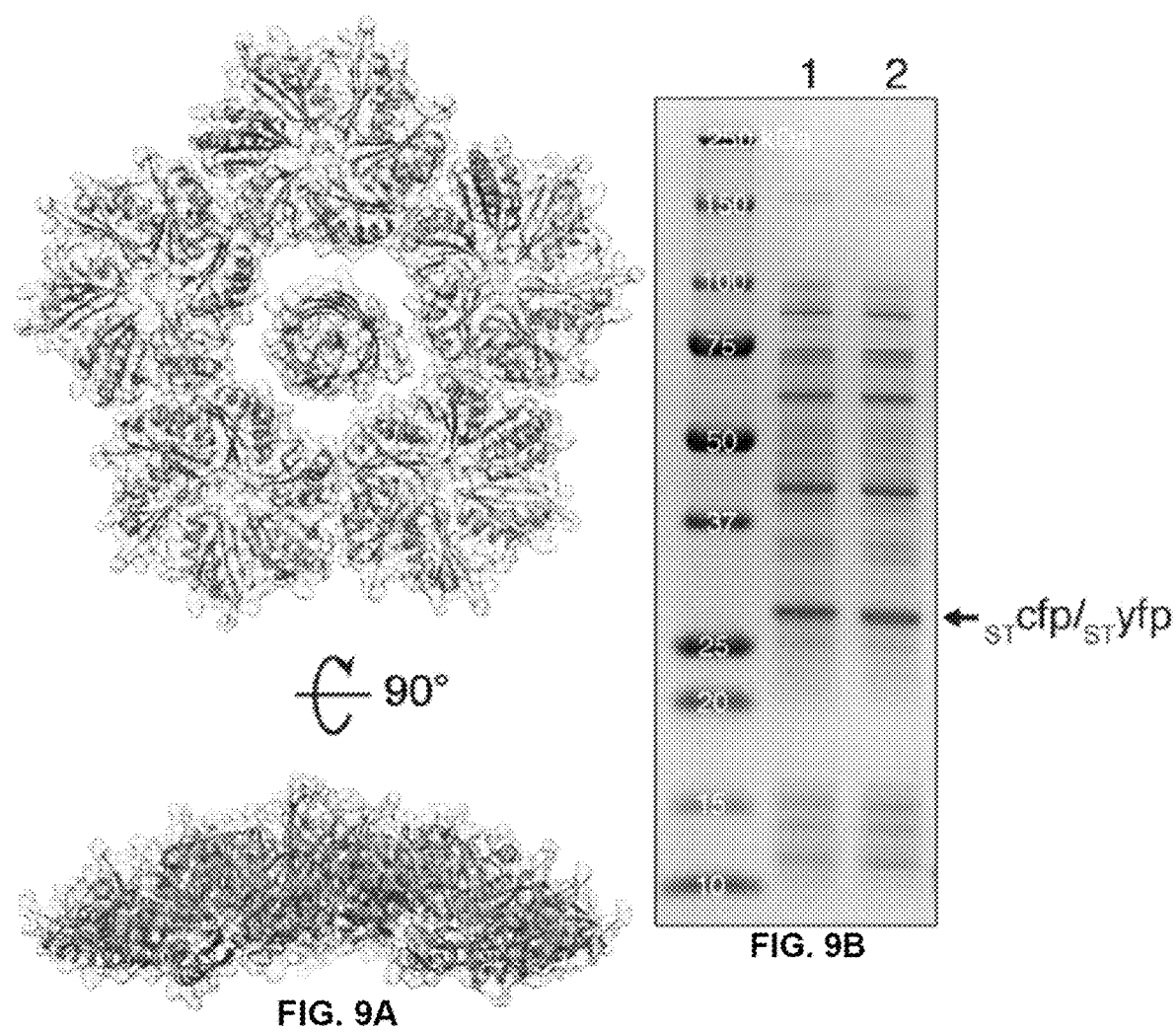
FIG. 9A shows molecular modeling of mTurquoise2 in pentamer vacancy. Model derived from Sutter 2017 depicting five hexamer subunits that abut HO shell pentamers with mTurquoise2 placed in pentamer void. Top: View from outside of the shell. Bottom: Side view.
FIG. 9B shows $_{ST}$cfp/$_{ST}$yfp expression. SDS-PAGE analysis of whole cell lysates. Lane 1: $_{ST}$cfp, Lane 2: $_{ST}$yfp.

Multiple Cargo Proteins Can Be Loaded Ex Vivo at Defined Ratios for Creation of Programmable Bacterial Microcompartments The in vivo encapsulation results do not allow us to distinguish between two non-mutually exclusive scenarios: $T_{SC/ST}$~cargo conjugation occurs prior to integration into proto-shells, or empty shells form first and cargo then conjugates to the trimer subunits after entry through the pentamer holes. The pentamer vacancies are ~47 Å diameter and can accomodate mTurquoise2 (FIG. 9A). We tested whether cargo could be loaded into pre-formed shells ex vivo by mixing clarified lysates of strains expressing $HT_{SC}$ shells with clarified lysates containing the previously described $_{ST}$cfp as well as SpyTagged yellow fluorescent protein, SYFP2 (24) ("$_{ST}$yfp") at varying volumetric ratios. These two fluorophores are spectrally well-matched as a Förster resonance energy transfer (FRET) pair (23) and therefore their co-localization is detectable spectrophotometrically. Expression under identical conditions in separate strains results in the same abundance of the $_{ST}$cfp and $_{ST}$yfp proteins in whole cell lysates (FIG. 9B).

Figures 5A, 5B:
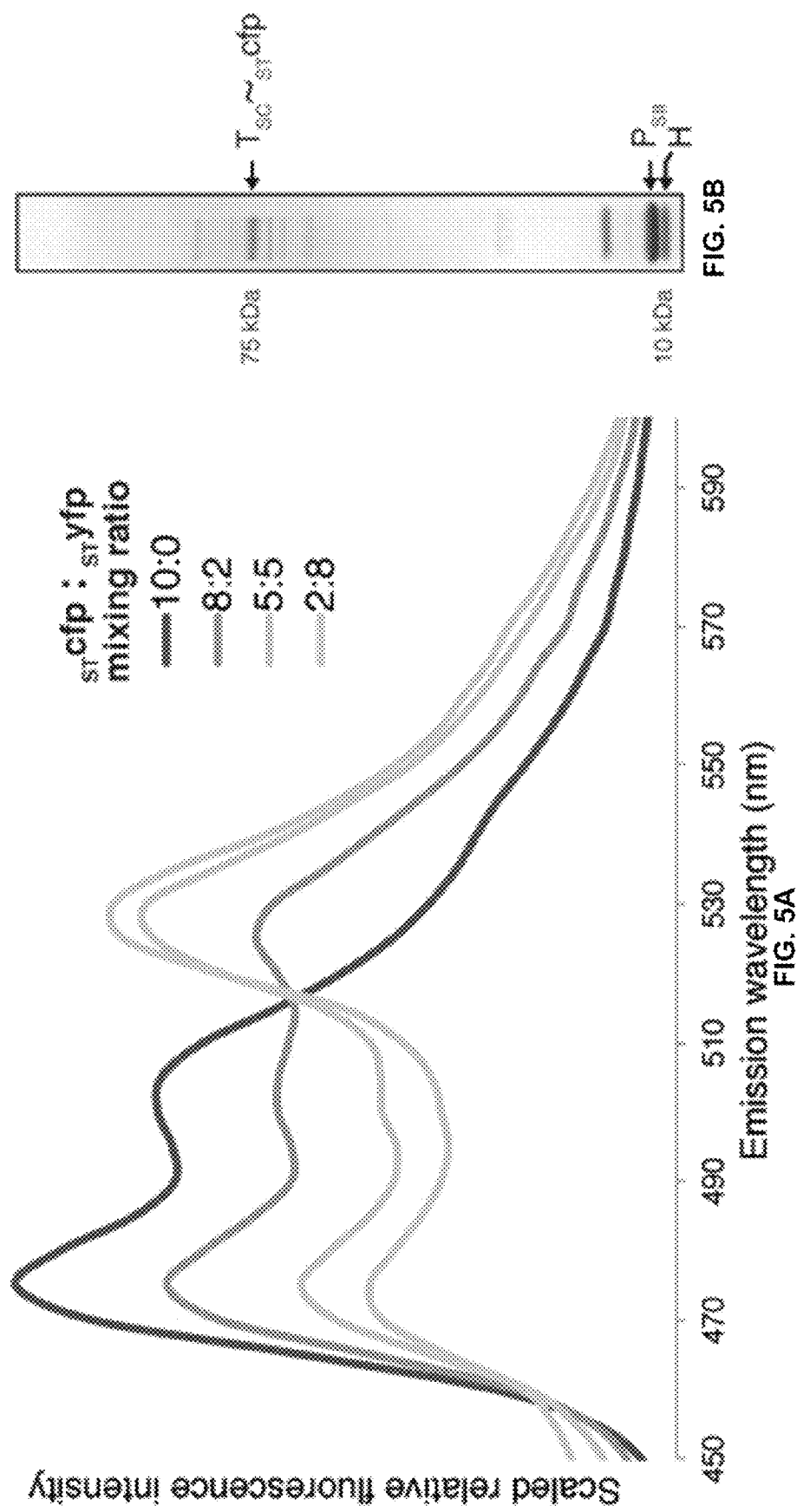
FIG. 5A shows the fluorescence spectra of shells containing ex vivo programmed cargo. Scaled emission spectra (excitation: 405 nm) of programmed cargo. $_{ST}$yfp only trace (0:10) was not plotted—in the absence of a FRET donor, the fluorescence signal is negligible.
FIG. 5B shows the SDS-PAGE analysis of shells containing ex vivo programmed cargo.

After cargo loading, the mixtures were subjected to CAP and analyzed spectrophotometrically; flow-through fractions which contain unencapsulated $_{ST}$cfp/$_{ST}$yfp were also collected for comparison. Shells were excited at 405 nm (a wavelength capable of $_{ST}$cfp excitation with negligible excitation of $_{ST}$yfp) and emission spectra was collected from 450 to 600 nm. As shown in FIG. 5A, increasing the proportion of $_{ST}$yfp in the mixture attenuates the emission of $_{ST}$cfp (emission maximum 474 nm) with a concomitant increase in emission from $_{ST}$yfp (emission maximum 527 nm) indicating FRET and co-localization of the two fluorophores. Control experiments comparing the fluorescence intensities of the two fluorophores in the shell preps and flow-through fractions corroborate these emission scan data (FIG. 10). Finally, the encapsulation efficiency of ex vivo cargo loading was assessed by SDS-PAGE analysis and no unconjugated $T_{SC}$ protein was detected (FIG. 5B). These data demonstrate that $_{ST}$cfp and $_{ST}$yfp co-localization is mediated by co-encapsulation within $HT_{SC}$ shells and that multi-cargo relative abundances can be robustly and easily programmed via ex vivo encapsulation—an important consideration for optimizing flux through multi-enzyme cascades and which is not readily achievable in vivo without laborious optimization of cargo expression levels.

Interrogation of HO Shell Permeability Using a FRET Based Sensor

Figure 6A:
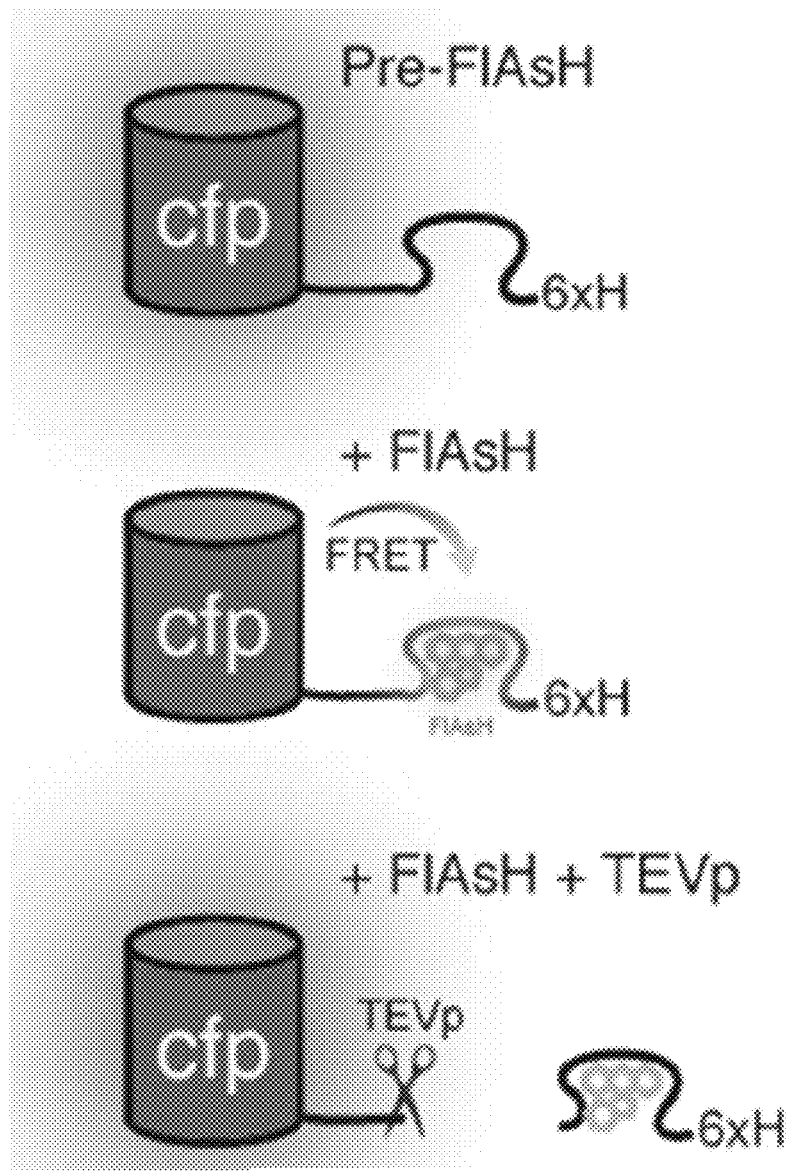
FIG. 6A shows the probe properties and permeability assay of uncapped and capped shells. Schematic of probe behavior in presence of FlAsH and TEV protease.
Figure 6B:
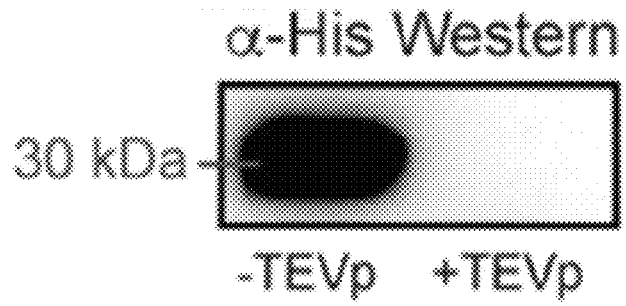
FIG. 6B shows the probe properties and permeability assay of uncapped and capped shells. Fluorescence emission spectra (excitation: 405 nm) of unencapsulated probe. Axis numbers omitted for clarity; tick marks correspond to numbers in FIG. 6B.
Figure 6C:
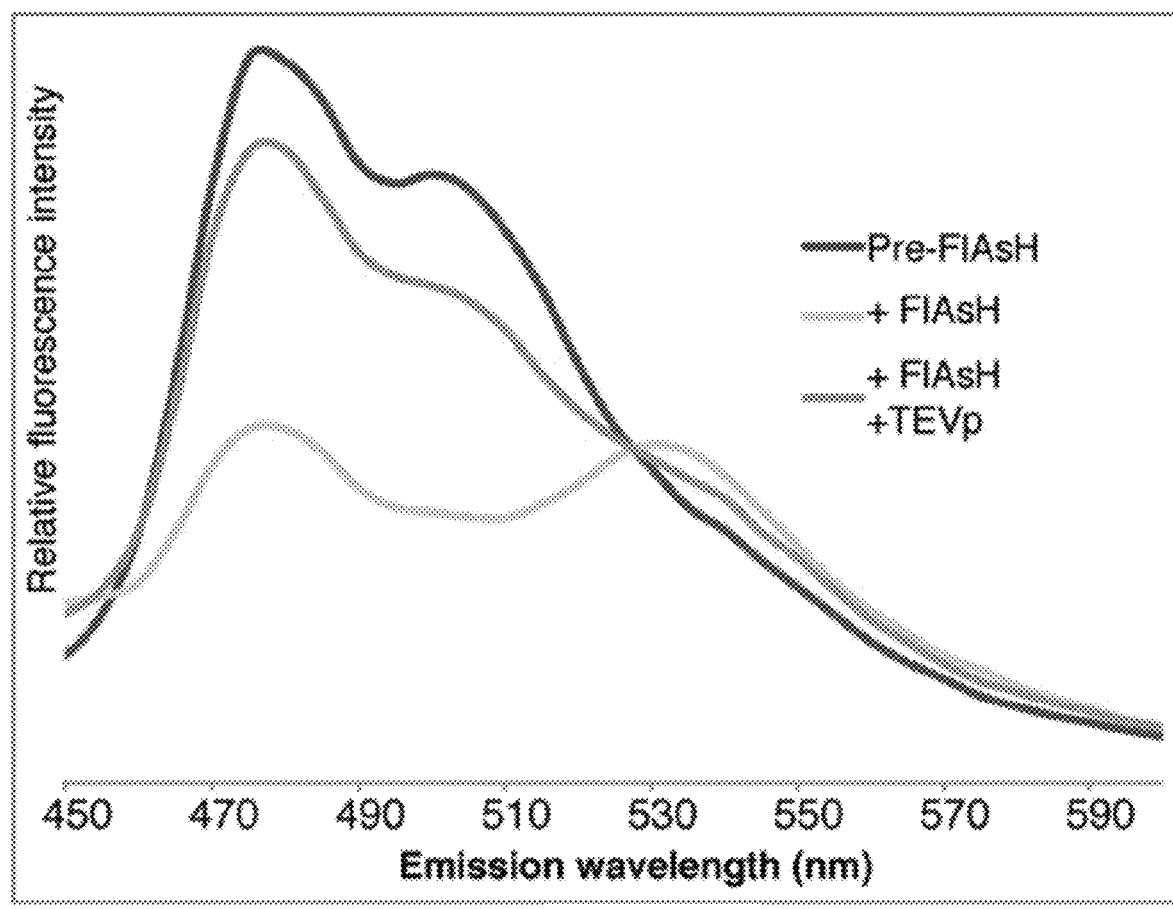
FIG. 6C shows the probe properties and permeability assay of uncapped and capped shells. anti-His Western blot against unencapsulated probe in absence and presence of TEVp. Axis numbers omitted for clarity; tick marks correspond to numbers in FIG. 6B.

A distinguishing feature of BMCs as compared to other proteinaceous compartments is selective permeability to an array of molecules—the identities of which depend on the particular native physiological function of a given BMC. The uncapped HO shells admit macromolecular species yet should prevent their entry/egress when fully capped. To test this behavior and confirm that CAP results in fully-complemented shells, we developed a FRET-based permeability probe and apply it towards elucidating the permeability of HO shells to protein and small molecule size scales. The tobacco etch virus protease (TEVp) cleavage site (25) followed by a six-residue tetracysteine motif was inserted between the C-terminus of mTurquoise2 and the hexahistidine tag of the $_{ST}$cfp construct to create the SpyTagged permeability probe, "$_{ST}$probe." Tetracysteine motifs tightly and specifically bind conditionally fluorescent biarsenical dyes such as the fluorescein-derived FlAsH reagent (26). At 664.5 Da, the FlAsH reagent is in a similar size regime as cofactors like NAD(P)H (744.4 Da) and therefore may be admitted through some subunit pores (5, 27, 28). The spectral properties of FlAsH are similar to SYFP2; binding to $_{ST}$probe positions the fluorophore within the Förster distance of mTurquoise2 and therefore this event can be detected spectrophotometrically. The spectral shift can subsequently be reversed by proteolytic removal of the labeled tetracysteine motif using TEVp. $_{ST}$probe's design and spectrophotometric behavior in response to incubation with FlAsH and TEVp when unencapsulated are depicted in FIG. 6A and FIG. 6B. Because TEVp also removes the C-terminal hexahistidine tag from the probe, cleavage can also be detected using western blotting against this epitope (FIG. 6C).

Figure 6D:
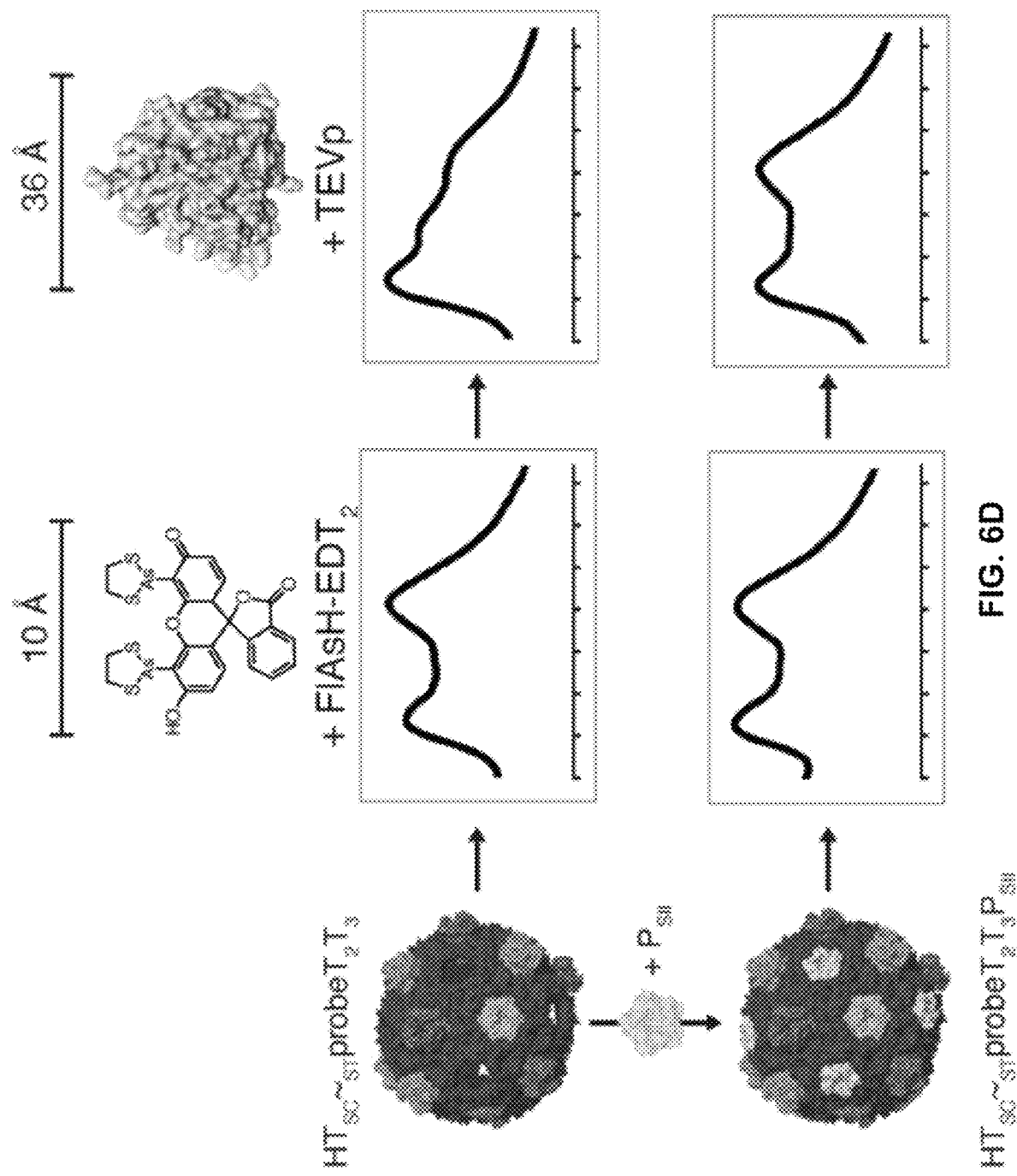
FIG. 6D shows the probe properties and permeability assay of uncapped and capped shells. Emission spectra (450 to 600 nm) of encapsulated probe in uncapped and capped shells, in the presence of FlAsH and TEV protease. Axis numbers omitted for clarity; tick marks correspond to numbers in FIG. 6B.
Figure 11A:
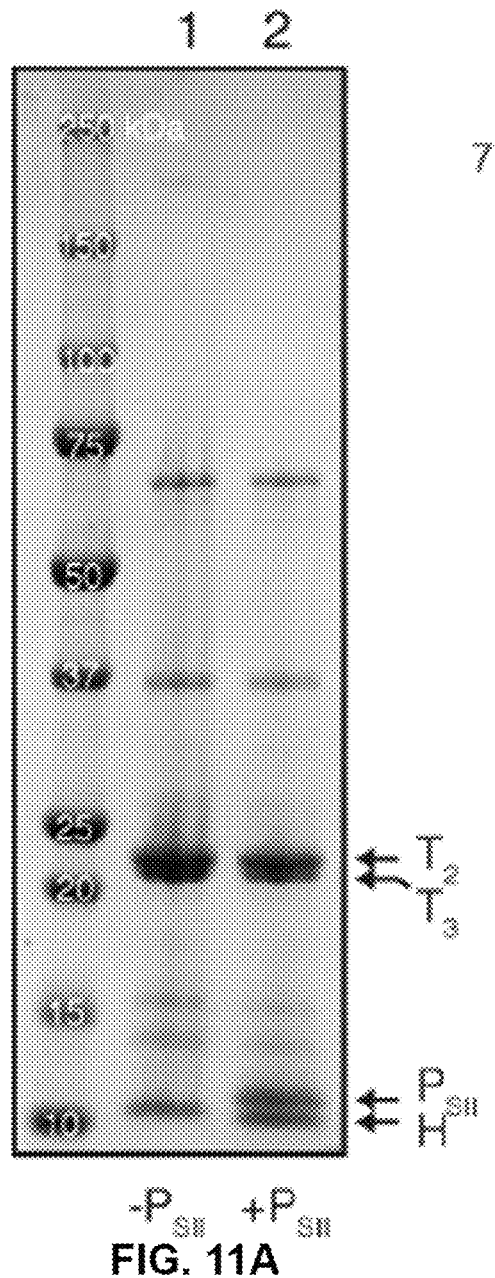
FIG. 11A shows the SDS-PAGE analysis of samples at conclusion of permeability experiment. SDS-PAGE of uncapped shells (lane 1) and capped shells (lane 2).
Figure 11B:
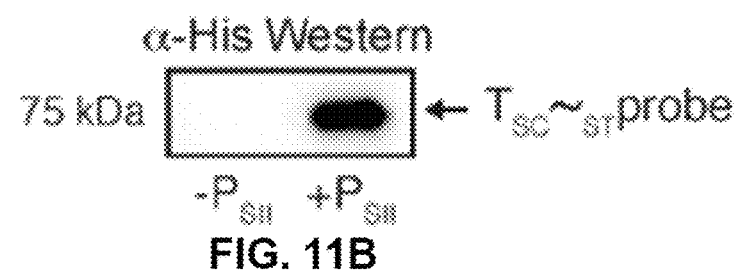
FIG. 11B shows the western blot of samples at conclusion of permeability experiment. anti-His western blot of the same reactions.

We performed a classical shell preparation of $_{ST}$probe-loaded, uncapped shells ($HT_{SC}$~$_{ST}$probe$T_2T_3$). Addition of the FlAsH reagent to the shells results in a fluorescence emission shift which is reverted upon TEVp addition (FIG. 6D, top row), recapitulating the behavior of unencapsulated probe. This demonstrates, as expected, that FlAsH and TEVp (approximately 36 Å in diameter) can enter the shells and proteolyze with the encapsulated probe. We next show that shells pre-capped via incubation with purified pentamer ($HT_{SC}$~$_{ST}$probe$T_2T_3P_{SH}$) still undergo a spectral shift when FlAsH is added, yet show no reversion in spectral emission upon addition of TEVp (FIG. 6D, bottom row). Exclusion of TEVp from these capped shells is confirmed by western blot analysis (FIG. 11A and FIG. 11B) and control experiments show that the pentamers themselves have no inhibitory effect on TEVp function (data not shown). We conclude that addition of the pentamer to uncapped shells is necessary and sufficient to preclude the entry of TEVp, though interestingly, these capped shells remain permeable to the FlAsH reagent, indicating it may be entering through the pores of one or more subunits. By leveraging EnCo for encapsulation of a novel permeability probe, these data indicate that CAP yields fully complemented shells with no unoccupied pentamer positions.

Discussion

In this study, we have elaborated the function of bacterial microcompartment shell proteins through the introduction of affinity handles and molecular traps. Complementation-based affinity purification (CAP) enables rapid purification of shells and by extension, screening for the formation of particles comprising varying subunits. Encapsulation via covalent-linkage (EnCo) allows facile programming of cargo composition expressed in cis and in trans. Using a novel permeability probe, we unambiguously demonstrate that shells capped in trans are fully complemented barriers against the transit of a macromolecular species (TEV protease) and yet admit the small molecule, FlAsH-EDT$_2$—likely through one or more of the distinct types of pores found in the shell proteins.

Previous work has shown that other BMCs such as the carboxysome can form without pentamers, though aberrant structures were observed microscopically in cells (6, 10, 29). In contrast, we observe no structural polymorphisms in HO shell preparations when pentamers are absent. Moreover, the isolation of morphologically undisrupted "minimal shells," each harboring a single trimer species, implies redundancy at the structural level while differing pore and stacking configurations implicate non-redundant functions in selective molecular transport across the shell. The ability to form uncapped shells enables the encapsulation of cargo ex vivo. As demonstrated, this allows multiple cargo species (which need not be expressed in the shell host) to be introduced into the shells at programmed ratios. Trapping SpyTag/Spy-Catcher-fused cargo in shells via EnCo is simple and efficient, however in principle any species able to transit the 47 Å diameter pentamer gap could be captured via co-incubation and capping. Such "stochastic encapsulation" would be of particular use in encapsulating molecules which cannot be tagged (e.g. acyl-CoA substrates), or even wholly abiotic materials.

Although there is a report of affinity enrichment of bacterial microcompartments (30), the resultant particles were heterogeneous and morphologically aberrant. This may be attributable to appending hexahistidine tags to multiple shell proteins which may sterically frustrate proper assembly. In contrast, the lack of any pentamer-pentamer subunit interactions in assembled shells advantages the use of this building block for embelishments and we have demonstrated that sixty Strep-II tags per particle provide sufficient avidity to pull-down highly pure shells. The isolation of beta-carboxysomal (Halo) shells demonstrates that this affinity pull-down strategy is applicable to other microcompartments that frequently exhibit morphological heterogeneity. Given the homology among the shell proteins of all BMCs, we expect that this method, after identifying specific combinations of subunits to form synthetic shells, will be generally applicable to other BMC systems.

The observations by us and others that encapsulation peptides are often ineffective at recruiting heterologous cargo to the lumen of BMC shells motivated us to pursue alternative means of encapsulation. Strategies for nanoparticle encapsulation such as engineering complementary electrostatics have proven useful for other nanocontainers such as lumazine synthase (31). However, this approach is not targeted and may non-specifically package resident charged molecules (e.g. nucleic acids) when performed in vivo. The SpyTag/SpyCatcher system has been used for encapsulation in other nanocompartments such as MS2 viral capsids and excitingly, encapsulated enzymes were shown to be more robust (32). However MS2 viral capsids are composed of a single protein type, and therefore lack any potential for compositional plasticity, which may decrease their utility. We believe that shared architectural features and structurally homologous insertion sites will allow translation of the SpyCatcher/SpyTag system to other BMC types. Moreover, despite the demonstrated superiority of EnCo to existing technology, improvements may be realized with additional protein engineering. For example alternatives to the currently employed poly-G/S linkers that flank SpyTag/SpyCatcher could improve solubility, cargo recruitment and integration into shells.

While numerous studies have demonstrated that the permeability of BMCs can be altered via rational mutagenesis of pore-lining residues, or even whole-sale swapping of subunits from one BMC system to another (33-35), assessing BMC permeability to a given small molecule is non-trivial, much less elucidating the permeability of specific subunits to said molecule. Our fluorescence-based probe serves as proof-of-principle for the use of these shell protein functionalizations for assessing shell permeability to small molecules in real time. In principle, any encapsulated enzymatic transformation(s) that results in a spectroscopic signal could serve as a readout of shell permeability, enabling the characterization of shell permeability to physiologically relevant species such as NAD(P)H. Leveraging the plasticity of subunit composition combined with altered selectivity from pore mutagenesis could allow for the facile creation of shells with bespoke permeabilities—likely a vital step towards increasing efficiencies of encapsulated, non-native pathways. The development of the EnCo and CAP methods represent significant steps towards more accessible physiological studies as well as realizing the biotechnological promises of bacterial microcompartments.

Methods

Shell Expression

BL21(DE3) strains harboring shell plasmids were grown to OD600 0.6-0.8 in lysogeny broth at 37° C. with 100 µg/ml ampicillin and induced with 50 µM IPTG with a brief cold-shock on ice. When co-expressing SpyTag/SpyCatcher cargo or $P_{SH}$, strains were additionally cultured with 50 µg/ml kanamycin and induced simultaneously with 5 ng/ml anhydrotetracycline. Incubation was then continued at 18° C. for 16-20 hours.

"Classical" Shell Purifications

Shells were prepared using methods described in[2]. Briefly, the cell pellet from a 2 L culture expressing $pHT_1T_2T_3$ was resuspended in Tris-buffered saline (20 mM Tris, 50 mM NaCl, pH 7.4 "TBS 20/50" hereafter), lysed by French press and clarified by centrifugation at 25,000×g for 30 minutes. After sucrose cushion and sucrose gradient centrifugations, shells were further purified by application to a MonoQ 10/100 GL anion-exchange column connected to an Äkta Pure system and elution with a shallow sodium chloride gradient (200-400 mM NaCl over 10 column volumes). Shell containing fractions were pooled and concentrated with a 15 ml 100 kDa MWCO filter (Amicon) and stored on ice after the addition of 0.02% sodium azide as a preservative. For $HT_{SC}$~$_{ST}$probeT$_2$T$_3$ shells, classically purified $HT_{SC}T_2T_3$ shells were incubated overnight with an excess of purified $_{ST}$probe (see supplementary methods) at 4° C. and then excess $_{ST}$probe was removed via application to a HisTrap column, followed by another MonoQ step. All buffers for the $HT_{SC}$~$_{ST}$probeT$_2$T$_3$ shell preparation were amended with 5 mM EDTA and 5 mM TCEP to maintain reducing conditions.

Complementation-Based Affinity Purification (CAP)

For initial in vivo and ex vivo capping, cell pellets from 1 L pHTTT culture were lysed using BPER-II amended with recombinant lysozyme and benzonase according to manufacturer's recommendation and clarified by centrifugation as above. Shell lysates were then mixed with clarified $P_{SH}$ lysates (2:1 v/v ratio of shell to pentamer pellets for $HT_1T_2T_3$ shells; 10:1 for all "minimal shells"; see methods for description of $P_{SH}$ expression) and incubated for thirty minutes to allow capping to occur. Lysates were then applied to a 5 ml StrepTrap (GE Healthcare) column equilibrated with Buffer A (100 mM Tris-HCl pH 7.4, 150 mM NaCl, 1 mM EDTA). The column was washed with six column volumes Buffer A and proteins were eluted in Buffer B (20 mM Tris-HCl pH 7.4, 50 mM NaCl, 1 mM EDTA, 2.5 mM D-desthiobiotin). Where specified, shells were further purified with anion-exchange chromatography and/or concentrated with 100 kDa molecular weight cut-off Amicon spin filters as described. Capping experiments involving encapsulated cargo (FIGS. 4A, 4B, 5A and 5B) were scaled down to 0.2 L shell cultures and purified with 1 ml StrepTrap columns using otherwise identical methods.

Pentamer Titration

Ex vivo capping was performed as described above except a range of clarified $P_{SH}$ lysate amounts (25, 10, 2.5, 1.25 and 0 ml) was added to 0.2 L equivalents $pHT_1T_2T_3$ shell lysate.

Ex Vivo Loading of $_{ST}$CFP/$_{ST}$YFP and $_{ST}$CFP into Minimal Shells

Cultures of pET11n::HT$_{SC/ST}$, pBbA2k::$_{ST/SC}$mTurquoise2-6×His and pBbA2k::$_{ST}$SYFP2-6×His were induced with 50 µM IPTG (pET11n::HT$_{SC/ST}$) or 50 ng/ml aTc (pBbA2k::$_{ST/SC}$mTurquoise2-6×His, pBbA2k::$_{ST}$SYFP2-6×His). Cell pellets were resuspended in Buffer A (4 ml per gram cell paste) supplemented with 12 µl benzonase (25 U/µl), a pinch of hen egg lysozyme and one Roche Complete EDTA-free protease inhibitor tablet, lysed using a French press and clarified by centrifugation as described. For co-encapsulation experiments, 0.2 L equivalents of the $HT_{SC}$ expressing lysate was mixed with a total of 0.2 L equivalent $_{ST}$cfpCFP/$_{ST}$yfpYFP lysates at varying ratios where one "part" corresponds to 20 ml lysate. For encapsulation of a single species (control reactions and loading into $HT_{ST}$ shells), 0.2 L equiv. of shell lysate was mixed with 0.2 ml equiv. cargo. Mixtures were incubated at room temperature overnight and then incubated with clarified $P_{SH}$ lysate and purified via 1 ml StrepTrap columns as described. For fluorescence comparisons to encapsulated $_{ST}$cfpCFP/$_{ST}$YFPyfp, the flow-through during sample application to the columns was collected. Shell eluates (6 ml) were concentrated with 100 kDa MWCO filters and diluted to equivalent volumes prior to fluorescence readings.

Permeability Experiments with FlAsH-EDT$_2$ and TEVp $HT_{SC}$~$_{ST}$probeT$_2$T$_3$ preps (final protein concentration of ~1 mg/ml) or unencapsulated $_{ST}$probe (~100 µg/ml) in 50 mM Tris-HCl pH 7.4, 150 mM NaCl, 5 mM EDTA, 5 mM TCEP, 1 mM β-mercaptoethanol were incubated in the absence or presence of excess $P_{SH}$ in microtiter plates for sixty minutes. A FlAsH-EDT$_2$ and 2,3-dimercapto-1-propanol solution (1 mM and 9 mM, respectively in DMSO) was added such that the final FlAsH-EDT$_2$ concentration was 10 µM and incubated at room temperature for 2 h. TEV protease was then added to a final concentration of 40 µg/ml and incubated for 2 h.

Chemicals and Reagents

FlAsH-EDT$_2$ was purchased from Carbosynth (Compton, United Kingdom), all other chemicals were purchased from Millipore-Sigma (St. Louis, USA).

SDS-PAGE Analysis of Shell Preparations

Shell preparations were normalized to A280=1, denatured in reducing sample buffer and loaded on 4-20% Mini-PROTEAN® TGX™ Precast Protein Gels (Bio-Rad, USA). Gels were washed and stained with SimplyBlue™ SafeStain (Thermo Fisher, USA); imaged with ChemiDoc™ XRS+ System and annotated with Image Lab™ Software (Bio-Rad).

Expression and Purification of $P_{SH}$ Protein

BL21(DE3)/pBbE2k::$P_{SH}$ strain was grown to OD600 0.6-0.8 at 37° C., induced with 50 ng/ml anhydrotetracycline (aTc) and harvested after an additional 4-6 h incubation at 37° C. Pellets were lysed with BPER-II as above. Insoluble debris was cleared via centrifugation and the supernatant applied to 5 ml StrepTrap (GE Healthcare) column equilibrated with Buffer A. The column was washed with 30 ml Buffer A and proteins were eluted in Buffer A supplemented with 2.5 mM D-desthiobiotin. Eluate was concentrated with 30 kDa molecular weight cut-off filters (Amicon) and further purified and buffer exchanged into 20 mM Tris-HCl pH 7.4, 50 mM NaCl via size-exclusion chromatography (HiLoad 16/600 Superdex 75 prep grade, GE Healthcare).

Expression and Purification of $_{ST}$Probe Protein

BL21(DE3)/pProbe strain was cultured and induced as with the $P_{SH}$ preparation. Cells were lysed by French press and 20 mM imidazole and 2.5 mM TCEP was added to clarified lysate and applied to a 5 ml HisTrap column (GE Healthcare) equilibrated with Buffer C (20 mM Tris-HCl pH 7.4, 300 mM NaCl, 20 mM imidazole, 2.5 mM TCEP). Column was washed with 10 column volumes Buffer C and eluted in a small volume with Buffer D (20 mM Tris-HCl pH 7.4, 300 mM NaCl, 100 mM imidazole, 2.5 mM TCEP). 5 mM EDTA, and 5 mM additional TCEP were added to eluate which was then further purified and buffer exchanged into 20 mM Tris-HCl pH 7.4, 50 mM NaCl, 5 mM EDTA, 5 mM TCEP via size-exclusion chromatography (HiLoad 16/600 Superdex 75 prep grade, GE Healthcare).

Shell Expression and "Classical" Purifications

BL21(DE3) strains harboring shell plasmids were grown to OD600 0.6-0.8 in lysogeny broth at 37° C. with 100 µg/ml ampicillin and induced with 50 uM IPTG with a brief cold-shock on ice. When co-expressing SpyTag/SpyCatcher cargo or $P_{SH}$, strains were additionally cultured with 50 µg/ml kanamycin and induced with 5 ng/ml anhydrotetracycline. Incubation was then continued at 18° C. for 16-20 hours. For "classical" shell preps using density gradient ultracentrifugation, methods described in (2) were followed except in the case of $HT_{SC}$~$_{ST}$probe$T_2T_3$ prep in which buffers were amended with 1 mM EDTA, 1 mM β-mercaptoethanol (BME) and 5 mM TCEP to maintain reducing conditions. When specified, shell preparations were further purified by application to a MonoQ anion-exchange column and elution over a shallow sodium chloride gradient as previously described (2). Shell containing fractions were pooled and concentrated with a 15 ml 100 kDa MWCO filter (Amicon) and stored on ice after the addition of 0.02% sodium azide as a preservative. For $HT_{SC}$~$_{ST}$probe$T_2T_3$ shells, classically purified $HT_{SC}T_2T_3$ shells were incubated overnight with an excess of purified $_{ST}$probe (see below) at 4° C. and then excess $_{ST}$probe was removed via application to a HisTrap column, followed by another MonoQ step. All other shell preps were performed in parallel for each given experiment at 200 ml culture scale using 1 ml StrepTrap columns with all lysis and buffer volumes scaled down accordingly and the MonoQ polishing step omitted. These eluates were concentrated with 0.5 ml 100 kDa MWCO filters.

TEV Protease Purification

TEV protease was purified using the protocol described in (38).

Fluorescence Intensity, Spectra Readings and Fluorescence Normalization

An M1000 plate reader (Tecan, Switzerland) was used to collect all fluorescence measurements in 96-well microplates with 50-100 µl of sample per well, in top-mode. Fluorescence intensity readings were collected with excitation and emission bandwidths of 5 nm; 430/475 nm for CFP and 515/530 nm for YFP. Emission spectra scans were collected via excitation at 405 nm and emission collection from 450 to 600 nm using 5 nm steps. For each individual experiment and fluorophore, the gain was optimized automatically to the well with the highest fluorescence value to avoid saturating the detector. For the $_{ST}$cfp/$_{ST}$yfp ex vivo loading experiment, the fluorescence intensity values for CFP only and YFP only (10:0 and 0:10, respectively) samples were normalized to 100 and all other values scaled according to the same factor. Emission spectra scans were normalized to total fluorescence emission (i.e. area under the curve of the emission scan from 450-600 nm) as the total fluorescence signal varied widely due to the differing amounts of FRET acceptor ($_{ST}$cfp) present in each sample.

Molecular Modeling and Images

UCSF Chimera (39) and PyMol (The PyMOL Molecular Graphics System, Version 2.0 Schrödinger, LLC.) were used for molecular visualizations and figure creation. To create the $T_{SC}$ model, the original atomic coordinates of HO BMC-T1 (PDB: 5DIH) were retrieved and the "GASGA" linker was deleted to split the chain into two fragments. The poly-G/S linker was made de novo using Chimera's build function and concatenated to BMC-T$_1$ fragment 1. The SpyCatcher atomic coordinates (PDB: 4MLI) were retrieved and trimmed appropriately to make the ΔN1AC2 variant which was then concatenated to the poly-G/S linker. The second poly-G/S linker was made as before and appended to the SpyCatcher domain. Bonds in the poly-G/S linkers were manually torsioned to juxtapose the C-terminus of the second poly-G/S linker to the N-terminus of the second BMC-T1 fragment and a peptide bond created between the two. The $T_{ST}$ model was made by replacing the SpyCatcher domain in the $T_{SC}$ model with a de novo generated SpyTag modeled as a beta-strand. The structures were imported into FoldIt (40) and allowed to minimize through side-chain and backbone "wiggling" with some manual guidance.

Electron Microscopy

For TEM analysis, 6 µl of purified shells at an A280 between 0.1-1 were mounted on formvar/carbon-coated copper grids (Electron Microscopy Sciences, No. 456 FCF300-Cu) for 30 seconds and then wicked away with filter paper. The grids were washed three times in 6 µl drops of water, dried with filter paper and then negatively stained with 5 µl 1% (w/v) aqueous uranyl acetate. After ten seconds, the stain was wicked off and the grids allowed to dry. Images were taken on a Tecnai 12 TEM operated at an accelerating voltage of 120 kV using an Ultrascan 1000 2 k×2 k CCD camera.

TABLE 1

Plasmid Construction

| Alias | Plasmid identity | Notes |
|---|---|---|
| pHT$_1$T$_2$T$_3$ | pET11n::HT$_1$T$_2$T$_3$ | Described in Sutter et al 2017 (41) |
| pARH292 | pBbE2k::P$_{SH}$ | Pentamer Hoch5814 was PCR amplified from the *Haliangium ochraceum* synthetic operon (42) to include a C-terminal Strep-II tag and cloned into pBbE2k (43) |
| pARH329 | pET11n::HT$_1$ | Inverse PCR was used to delete trimers T$_2$ and T$_3$ (Hoch5816 and Hoch3341, respectively) from pHT$_1$T$_2$T$_3$ |
| pARH317 | pET11n::HT$_2$ | Inverse PCR was used to delete trimers T$_1$ and T$_3$ (Hoch5812 and Hoch3341, respectively) from pHT$_1$T$_2$T$_3$ |
| pARH387 | pET11n::HT$_3$ | Gibson assembly was used to remove trimers T$_1$ and T$_2$ (Hoch5812 and Hoch5816, respectively) from pHT$_1$T$_2$T$_3$ |

TABLE 1-continued

Plasmid Construction

| Alias | Plasmid identity | Notes |
| --- | --- | --- |
| pARH346 | pET11n::HT$_{ST}$ | Inverse PCR was used to introduce the SpyTag sequence flanked by poly-Gly/Ser linkers into the T$_1$ (Hoch5812) domain of plasmid pARH329 after amino acid Gly84 (...AGAG[insertion]SGA...) |
| pARH349 | pET11n::3 | The same cloning strategy employed to create pARH346 was employed using pHT$_1$T$_2$T$_3$ as template |
| pARH353 | pET11n::HT$_{SC}$ | Gibson assembly (44) was used to replace the SpyTag region in pARH346 with the SpyCatcherΔN1ΔC2 variant domain (45) while maintaining the insulating poly-Gly/Ser linkers. |
| pARH355 | pET11n::HT$_{SC}$T$_2$T$_3$ | The same cloning strategy employed to create pARH353 was employed using pARH349 as template |
| pARH360 | pBbA2k::6 × His-$_{SC}$mTurquoise2 | Gibson assembly was used to introduce the 6 × His-SpyCatcher and an *E. coli* codon-optimized version of mTurquoise2 (Integrated DNA Technologies, Coralville USA; (46)) domains into pBbA2k (43) |
| pARH364 | pBbA2k::$_{ST}$mTurquoise2-6 × His | mTurquoise2 with an N-terminal 13 residue SpyTag and C-terminal hexahistidine tag was cloned into pBbA2k |
| pARH365 | pBbA2k::$_{ST}$SYFP2-6 × His | mTurquoise2 from pARH364 was replaced with an *E. coli* codon-optimized version of SYFP2 (Integrated DNA Technologies, Coralville USA; (47)) using Gibson assembly. |
| pARH389 | pBbA2k::SpyTag-mTurquoise2-tev-4 × C-6 × H ("pProbe") | Inverse PCR was used to introduce the canonical TEV protease cleavage site and the tetracysteine FlAsH binding site (CCPGCC), both flanked by poly-G/S linkers using pARH364 as template. |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for titrating a range of BMC shells with variable permeability, the method comprising:
   (a) determining a desired permeability for a BMC shell,
   (b) forming a series of BMC shells with a variable amount of a fusion protein, comprising a BMC-P and a first component, relative to the amounts of the BMC-H and BMC-T shell proteins, and
   (c) determining the permeability of each BMC shell formed with a specific amount of the fusion protein relative the amounts of the BMC-H and BMC-T shell proteins.

2. The method of claim 1, wherein the step (b) forming comprises using an in vivo capped or ex vivo capped method.

3. The method of claim 1, the method further comprising: purifying or isolating each BMC shell formed with a specific amount of the fusion protein relative the amounts of the BMC-H and BMC-T shell proteins using a second component bound to a solid support; wherein the purifying or isolating step occurs after the (b) forming step and prior to the (c) determining step.

4. The method of claim 1, the method further comprising:
(d) identifying the BMC shell of step (b) that has a permeability closest to the desired permeability determined in the determining a desired permeability for a BMC shell step.

5. The method of claim 1, wherein the fusion protein comprises: (1) a bacterial microcompartment (BMC) shell protein comprising one or more subunit, and (2) a first component of a specific-binding pair, operably linked to the BMC shell protein such that the first component faces (i) a lumen side, or (ii) outside of a BMC shell formed incorporating the fusion protein and the fusion protein does not disrupt or prevent the folding of the BMC shell protein or the ability of the BMC shell protein to integrate with other BMC shell proteins into a BMC shell; wherein the first component is capable of forming a stable or irreversible interaction with a second component of the specific-binding pair.

6. The method of claim 5, wherein the fusion protein comprises: (1) a bacterial microcompartment (BMC) shell protein comprising one or more subunit, and (2) a first component of a specific-binding pair, operably linked to the BMC shell protein such that the first component faces a lumen (inside) side, of a BMC shell formed incorporating the fusion protein and the fusion protein does not disrupt or prevent the folding of the BMC shell protein or the ability of the BMC shell protein to integrate with other BMC shell proteins into a BMC shell; wherein the first component is capable of forming a stable or irreversible interaction with a second component of the specific-binding pair.

7. The method of claim 5, wherein the fusion protein comprises: (1) a bacterial microcompartment (BMC) shell protein comprising one or more subunit, and (2) a first component of a specific-binding pair, operably linked to the BMC shell protein such that the first component faces outside of a BMC shell formed incorporating the fusion protein and the fusion protein does not disrupt or prevent the folding of the BMC shell protein or the ability of the BMC shell protein to integrate with other BMC shell proteins into a BMC shell; wherein the first component is capable of forming a stable or irreversible interaction with a second component of the specific-binding pair.

8. The method of claim 5, wherein the stable or irreversible interaction is a spontaneous formation of a covalent bond.

9. The method of claim 8, wherein the covalent bond is an isopeptide bond.

10. The method of claim 9, wherein (a) said first component is a peptide tag comprising a peptide fragment of an isopeptide protein, said tag having a length of at least 5 amino acids but no more than 50 amino acids, and comprises a first reactive residue involved in formation of an intramolecular isopeptide bond in an isopeptide protein, wherein said peptide tag is either unconjugated or is conjugated to a heterologous protein or peptide or to another molecule and wherein said isopeptide protein is selected from the group consisting of (i) major pilin protein Spy0128 from *Streptococcus pyogenes* as set forth in SEQ ID NO: 1 or a protein with at least 95% identity thereto capable of spontaneously forming an isopeptide bond, or (ii) FbaB from *S. pyogenes* as set forth in SEQ ID NO:2, or a protein with at least 80% identity thereto capable of spontaneously forming an isopeptide bond; (b) said binding partner (i) comprises a different fragment of an isopeptide protein as set forth in (a)(i) or (a)(ii) wherein said fragment is at least 20 amino acids in length and (ii) comprises a second reactive residue involved in the isopeptide bond in said isopeptide protein, wherein the binding partner does not include the first reactive residue of the peptide tag; and (c) said peptide tag and binding partner are capable of binding to each other and forming an isopeptide bond between the first and second reactive residues.

11. The method of claim 1, wherein the BMC shell protein of the fusion protein is a BMC shell protein comprising a domain which forms the pentagonal vertice of the BMC shell.

* * * * *

SEQUENCE LISTING

```
<160> NUMBER OF SEQ ID NOS: 7

<210> SEQ ID NO 1
<211> LENGTH: 340
<212> TYPE: PRT
<213> ORGANISM: Streptococcus pyogenes

<400> SEQUENCE: 1

Met Lys Leu Arg His Leu Leu Thr Gly Ala Ala Leu Thr Ser Phe
1               5                   10                  15

Ala Ala Thr Thr Val His Gly Glu Thr Val Val Asn Gly Ala Lys Leu
            20                  25                  30

Thr Val Thr Lys Asn Leu Asp Leu Val Asn Ser Asn Ala Leu Ile Pro
        35                  40                  45

Asn Thr Asp Phe Thr Phe Lys Ile Glu Pro Asp Thr Thr Val Asn Glu
    50                  55                  60

Asp Gly Asn Lys Phe Lys Gly Val Ala Leu Asn Thr Pro Met Thr Lys
65                  70                  75                  80

Val Thr Tyr Thr Asn Ser Asp Lys Gly Gly Ser Asn Thr Lys Thr Ala
            85                  90                  95

Glu Phe Asp Phe Ser Glu Val Thr Phe Glu Lys Pro Gly Val Tyr Tyr
        100                 105                 110

Tyr Lys Val Thr Glu Glu Lys Ile Asp Lys Val Pro Gly Val Ser Tyr
    115                 120                 125

Asp Thr Thr Ser Tyr Thr Val Gln Val His Val Leu Trp Asn Glu Glu
130                 135                 140
```

```
Gln Gln Lys Pro Val Ala Thr Tyr Ile Val Gly Tyr Lys Glu Gly Ser
145                 150                 155                 160

Lys Val Pro Ile Gln Phe Lys Asn Ser Leu Asp Ser Thr Thr Leu Thr
                165                 170                 175

Val Lys Lys Val Ser Gly Thr Gly Gly Asp Arg Ser Lys Asp Phe
            180                 185                 190

Asn Phe Gly Leu Thr Leu Lys Ala Asn Gln Tyr Tyr Lys Ala Ser Glu
            195                 200                 205

Lys Val Met Ile Glu Lys Thr Thr Lys Gly Gly Gln Ala Pro Val Gln
            210                 215                 220

Thr Glu Ala Ser Ile Asp Gln Leu Tyr His Phe Thr Leu Lys Asp Gly
225                 230                 235                 240

Glu Ser Ile Lys Val Thr Asn Leu Pro Val Gly Val Asp Tyr Val Val
                245                 250                 255

Thr Glu Asp Asp Tyr Lys Ser Glu Lys Tyr Thr Thr Asn Val Glu Val
                260                 265                 270

Ser Pro Gln Asp Gly Ala Val Lys Asn Ile Ala Gly Asn Ser Thr Glu
                275                 280                 285

Gln Glu Thr Ser Thr Asp Lys Asp Met Thr Ile Thr Phe Thr Asn Lys
            290                 295                 300

Lys Asp Phe Glu Val Pro Thr Gly Val Ala Met Thr Val Ala Pro Tyr
305                 310                 315                 320

Ile Ala Leu Gly Ile Val Ala Val Gly Gly Ala Leu Tyr Phe Val Lys
                325                 330                 335

Lys Lys Asn Ala
            340

<210> SEQ ID NO 2
<211> LENGTH: 102
<212> TYPE: PRT
<213> ORGANISM: Streptococcus pyogenes

<400> SEQUENCE: 2

Met Thr Ile Glu Glu Asp Ser Ala Thr His Ile Lys Phe Ser Lys Arg
1               5                   10                  15

Asp Ile Asp Gly Lys Glu Leu Ala Gly Ala Thr Met Glu Leu Arg Asp
                20                  25                  30

Ser Ser Gly Lys Thr Ile Ser Thr Trp Ile Ser Asp Gly Gln Val Lys
            35                  40                  45

Asp Phe Tyr Leu Met Pro Gly Lys Tyr Thr Phe Val Glu Thr Ala Ala
    50                  55                  60

Pro Asp Gly Tyr Glu Ile Ala Thr Ala Ile Thr Phe Thr Val Asn Glu
65                  70                  75                  80

Gln Gly Gln Val Thr Val Asn Gly Lys Ala Thr Lys Gly Asp Ala His
                85                  90                  95

Ile Val Met Val Asp Ala
            100

<210> SEQ ID NO 3
<211> LENGTH: 5
<212> TYPE: PRT
<213> ORGANISM: Haliangium ochraceum

<400> SEQUENCE: 3

Ala Gly Ser Gly Ala
1               5
```

<210> SEQ ID NO 4
<211> LENGTH: 99
<212> TYPE: PRT
<213> ORGANISM: Artificial Sequence
<220> FEATURE:
<223> OTHER INFORMATION: Synthesized bacterial microcompartment shell
    protein

<400> SEQUENCE: 4

```
Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Tyr Val Thr Ala Val Val Arg Gly
        35                  40                  45

Asp Val Ala Val Lys Ala Ala Thr Glu Ala Gly Gln Arg Ala Ala
    50                  55                  60

Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala
```

<210> SEQ ID NO 5
<211> LENGTH: 102
<212> TYPE: PRT
<213> ORGANISM: Artificial Sequence
<220> FEATURE:
<223> OTHER INFORMATION: Synthesized bacterial microcompartment shell
    protein

<400> SEQUENCE: 5

```
Met Glu Val Val Ala Val His Val Ile Pro Arg Pro His Val Asn Val
1               5                   10                  15

Asp Ala Ala Leu Pro Leu Gly Arg Thr Pro Gly Met Asp Lys Ser Ala
            20                  25                  30

Gly Ser Gly Ser Gly Ser Ala Asp Ala Leu Gly Met Ile Glu Val Arg
        35                  40                  45

Gly Phe Val Gly Met Val Glu Ala Ala Asp Ala Met Val Lys Ala Glu
    50                  55                  60

Leu Ile Gly Tyr Glu Lys Thr Gly Gly Tyr Val Thr Ala Val Val
65                  70                  75                  80

Arg Gly Asp Val Ala Val Lys Ala Ala Thr Glu Ala Gly Gln Arg
                85                  90                  95

Ala Ala Glu Arg Val Gly
            100
```

<210> SEQ ID NO 6
<211> LENGTH: 205
<212> TYPE: PRT
<213> ORGANISM: Artificial Sequence
<220> FEATURE:
<223> OTHER INFORMATION: Synthesized bacterial microcompartment shell
    protein

<400> SEQUENCE: 6

```
Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
```

```
                    20                  25                  30
Gly Ile Thr Val Ala Asp Ala Ala Leu Lys Arg Ala Pro Ser Leu Leu
                35                  40                  45

Leu Met Ser Arg Pro Val Ser Ser Gly Lys His Leu Leu Met Met Arg
        50                  55                  60

Gly Gln Val Ala Glu Val Glu Glu Ser Met Ile Ala Ala Arg Glu Ile
65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
                100                 105                 110

Ala Trp Glu Glu Asp Thr Glu Ser Val Ile Ile Val Glu Thr Ala Thr
            115                 120                 125

Val Cys Ala Ala Ile Asp Ser Ala Asp Ala Ala Leu Lys Thr Ala Pro
        130                 135                 140

Val Val Leu Arg Asp Met Arg Leu Ala Ile Gly Ile Ala Gly Lys Ala
145                 150                 155                 160

Phe Phe Thr Leu Thr Gly Glu Leu Ala Asp Val Glu Ala Ala Ala Glu
                165                 170                 175

Val Val Arg Glu Arg Cys Gly Ala Arg Leu Leu Glu Leu Ala Cys Ile
                180                 185                 190

Ala Arg Pro Val Asp Glu Leu Arg Gly Arg Leu Phe Phe
                195                 200                 205

<210> SEQ ID NO 7
<211> LENGTH: 96
<212> TYPE: PRT
<213> ORGANISM: Artificial Sequence
<220> FEATURE:
<223> OTHER INFORMATION: Synthesized bacterial microcompartment shell
      protein

<400> SEQUENCE: 7

Met Val Leu Gly Lys Val Val Gly Thr Val Val Ala Ser Arg Lys Glu
1               5                   10                  15

Pro Arg Ile Glu Gly Leu Ser Leu Leu Leu Val Arg Ala Cys Asp Pro
                20                  25                  30

Asp Gly Thr Pro Thr Gly Gly Ala Val Val Cys Ala Asp Ala Val Gly
            35                  40                  45

Ala Gly Val Gly Glu Val Val Leu Tyr Ala Ser Gly Ser Ser Ala Arg
    50                  55                  60

Gln Thr Glu Val Thr Asn Asn Arg Pro Val Asp Ala Thr Ile Met Ala
65                  70                  75                  80

Ile Val Asp Leu Val Glu Met Gly Gly Asp Val Arg Phe Arg Lys Asp
                85                  90                  95
```